United States Patent
Haerer et al.

(10) Patent No.: US 6,442,288 B1
(45) Date of Patent: Aug. 27, 2002

(54) METHOD FOR RECONSTRUCTING A THREE-DIMENSIONAL IMAGE OF AN OBJECT SCANNED IN THE CONTEXT OF A TOMOSYNTHESIS, AND APPARATUS FOR TOMOSYNTHESIS

(75) Inventors: Wolfgang Haerer, Erlangen; Guenter Lauritsch, Fuerth; Michael Zellerhoff, Sprockhoevel, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/207,125

(22) Filed: Dec. 7, 1998

(30) Foreign Application Priority Data

Dec. 17, 1997 (DE) .......................... 197 56 246
Sep. 18, 1998 (DE) .......................... 198 42 944

(51) Int. Cl.$^7$ ................................ G06K 9/00
(52) U.S. Cl. ........................ 382/128; 382/100
(58) Field of Search ........................ 382/128, 100; 128/922; 250/455.11; 600/409

(56) References Cited

U.S. PATENT DOCUMENTS

| 4,903,204 A | 2/1990 | Dobbins, III ............... 382/255 |
| 5,422,962 A * | 6/1995 | Yasukawa et al. .......... 382/295 |
| 5,489,782 A * | 2/1996 | Wernikoff ................. 250/369 |

(List continued on next page.)

OTHER PUBLICATIONS

"Tomosynthesis: A Three–Dimensional Radiographic Imaging Technique," Grant, IEEE Trans. on Biomed. Eng. vol. BME 19, No. 1 (Jan. 1972), pp. 20–28.

"Computerized Tomosynthesis of Dental Tissues," Groenhuis et al., Oral Surgery, vol. 56 (Aug. 1983), pp. 206–214.

"An Optimal Synthetic Aperture for Circular Tomosynthesis," Ruttiman et al., Med. Phys. vol. 16, No. 3 (May/Jun. 1989) pp. 398–405.

(List continued on next page.)

Primary Examiner—Leo Boudreau
Assistant Examiner—M B Choobin
(74) Attorney, Agent, or Firm—Schiff Hardin & Waite

(57) ABSTRACT

In a method for reconstruction of a three-dimensional image of an object scanned in linear or circular fashion in the context of a tomosynthesis. The object is transirradiated with X-rays from various projection angles $\phi$ for the recording of the projection images, and the radiation exiting from the object is recorded by a detector that supplies digital output image signals. The output image signals representing the projection image data are supplied to a computer for image reconstruction. In the context of the reconstruction a filter is first produced, on the basis of the following steps: A 3D transmission function $H_{proj}(\omega_x,\omega_y,\omega_z)$ is calculated from the recording geometry for the individual projection image recording and the back-projection of the individual projection images into the 3D reconstruction image volume. By approximation, the 3D transmission function $H_{proj}(\omega_x,\omega_y,\omega_z)$ is inverted for the determination of an inversion function $H_{inv}(\omega_x,\omega_y,\omega_z)$. A 3D filtering function $H_{opt}(\omega_x,\omega_y,\omega_z)$ is produced dependent on one or more desired image characteristics of the reconstruction image. A resulting 3D filtering function $H_{filter}(\omega_x,\omega_y,\omega_z)$ is determined by multiplication of the 3D filtering function $H_{opt}(\omega_x,\omega_y,\omega_z)$ and the inversion function $H_{inv}(\omega_x,\omega_y,\omega_z)$. A 2D filtering function $H^{2D}_{filter,\phi}(\omega_u,\omega_v)$ is determined from the resulting 3D filtering function $H_{filter}(\omega_u,\omega_v,\omega_z)$ by coordinate transformation of the 3D object space into the 2D projection image space of the respective individual projection images at the projection angle $\phi$. After calculating the filter, the reconstruction of the image takes place in the computer by application of the 2D filtering function $H^{2D}_{filter,\phi}(\omega_u,\omega_v)$ to the associated individual projection image data, and production of the reconstruction image by back-projection of the filtered individual projection image data, into the 3D reconstruction image volume.

50 Claims, 9 Drawing Sheets

U.S. PATENT DOCUMENTS

| | | | | |
|---|---|---|---|---|
| 5,699,440 A | * | 12/1997 | Carmeli | 382/100 |
| 5,737,456 A | * | 4/1998 | Carrington et al. | 382/299 |
| 6,058,322 A | * | 5/2000 | Nishikawa et al. | 600/408 |
| 6,101,263 A | * | 8/2000 | Shimizu et al. | 382/100 |
| 6,201,849 B1 | * | 3/2001 | Lai | 378/4 |

OTHER PUBLICATIONS

"Restoration of Digital Multiplane Tomosynthesis by a Constrained Iteration Method," Ruttimann et al., IEEE Trans. on Med. Imaging, Vol. MI–3, No. 3 (Sep. 1984), pp. 141–148).

"Three–Dimensional Image Reconstruction by Digital Tomosynthesis Using Inverse Filtering," Matsuo et al., IEEE Trans. on Med. Imaging, vol. 12, No. 2 (Jun. 1993), pp. 307–313.

"Ectomography: A New Radiographic Method for Reproducing a Selected Slice of Varying Thickness," Edholm et al., Acta Radiologica, vol. 21, No. 4 (1980), pp. 433k–442.

A Mobile Tomographic Gamma Camera System for Acute Studies, Dale et al., IEEE Trans. on Nuclear Sci., vol. 44, No. 2 (Apr. 1997), pp. 199–203.

* cited by examiner

METHOD FOR RECONSTRUCTING A THREE-DIMENSIONAL IMAGE OF AN OBJECT SCANNED IN THE CONTEXT OF A TOMOSYNTHESIS, AND APPARATUS FOR TOMOSYNTHESIS

BACKGROUND OF THE INVENTION

1. Field of the Invention

The invention relates to a method for reconstructing a three-dimensional image of an object or a subject scanned, preferably in linear or circular fashion, in the context of a tomosyntheisis procedure of the type wherein during the scanning, several individual projection images located in a 2D projection image space are recorded in the form of digital projection image data of the object located in a 3D object space, and are back-projected into a 3D reconstruction image volume in order to produce the reconstruction image, the object being irradiated with X-rays from various projection angles $\phi$ for the purpose of recording the projection images, and wherein the radiation exiting from the object is recorded using a detector that supplies digital output image signals, the output image signals representing the projection image data and being supplied to a computer for image reconstruction.

2. Description of the Prior Art

In medical imaging systems, it is known to record an object tomosynthetically and to reconstruct it three-dimensionally. Since in the tomosynthetic data recording the object to be imaged are projected onto a detector from only a few spatial directions, the object scanning is incomplete. This is expressed in a poor depth resolution of the 3D reconstruction. In a simple back-projection (identical to the summation of displaced projection images, classical slice method), without reconstructive corrections locus-frequency-dependent artefacts are contained in the tomograms. Given larger objects, these disturbances can be very extensive.

The following demands are placed on a good 3D reconstruction: best possible suppression of structures foreign to the slice, defined slice behavior or characteristic, i.e. depth resolution independent of locus frequency, purposive controlling of the characteristics of the reconstructed tomogram.

In system-theoretical terms, the tomosynthetic imaging of an object distribution $f(x, y, z)$ to form a 3D reconstruction image $g(x, y, z)$ can be formulated as a convolution (indicated, as is standard, by the symbol *) of the object distribution with the point image function $h(x, y, z)$ of the imaging process:

$$g(x, y, z) = h(x, y, z) * f(x, y, z)$$

The point image function $h(x, y, z)$ describes both the "measurement process" (projection and back-projection) and also reconstructive measures, such as e.g. filterings. In the 3D Fourier space, the Fourier-transformed image $G(\omega_x, \omega_y, \omega_z)$ is described by a multiplication of the Fourier-transformed object distribution $F(\omega_x, \omega_y, \omega_z)$ with the 3D transmission function (or Modulation Transfer Function MTF) $H(\omega_x, \omega_y, \omega_z)$:

$$G(\omega_x, \omega_y, \omega_z) = H(\omega_x, \omega_y, \omega_z) \cdot F(\omega_x, \omega_y, \omega_z)$$

with $F(\omega_x, \omega_y, \omega_z)$ as the 3D Fourier transformation of the locus distribution $f(x, y, z)$ $$F(\omega_x, \omega_y, \omega_z) = F_z F_y F_x f(x, y, z)$$

and analogously for the image $g(x, y, z)$ and the point image function $h(x, y, z)$. By modification of the point image function $h(x, y, z)$ or of the Modulation Transfer Function $H(\omega_x, \omega_y, \omega_z)$ the imaging process can be purposively influenced.

The image quality of a reconstructed tomogram can be judged using the slice transmission function $h(\omega_x, \omega_y | z)$ [D. G. Grant, TOMOSYNTHESIS: A Three-Dimensional Radiographic Imaging Technique, IEEE Trans. on Biomed. Eng. 19 (1972), 20–28].

$$h(\omega_x, \omega_y | z) = F_z^{-1} H(\omega_x, \omega_y, \omega_z)$$

The slice transmission function $h(\omega_x, \omega_y | z)$ is a hybrid of a representation in the Fourier space and in the locus space. It indicates the spectral content (frequency response) with which objects at a distance z from the reconstruction plane contribute to the reconstruction image. For z=0, it indicates the spectral content of the slice to be reconstructed, and for small z it indicates the screen characteristic of a reconstruction slice of finite thickness, and for large z, specifically in tomosynthesis, it indicates the locus-frequency-dependent feed-through of artefacts. The desired image characteristics (see above) can be formulated as follows using the slice transmission function.

A good suppression of structures foreign to the slice signifies a rapid decay of the slice transmission function $h(\omega_x, \omega_y | z)$ into z.

Defined slice behavior, i.e. a slice profile independent of the locus frequency, is achieved by a separation of the slice transmission function $h(\omega_x, \omega_y | z)$ into a portion $H_{spectrum}(\omega_x, \omega_y)$, which represents the spectral image content of the reconstructed tomogram, and into a portion $h_{profile}(z)$ that defines the slice profile. A complete separation is in general not possible in tomosynthesis, since as the locus frequencies decrease the scanning becomes increasingly incomplete. It is already a considerable advantage, however, if a separation is achieved for a limited locus frequency region:

$$h(\omega_x, \omega_y | z) = H_{spectrum}(\omega_x, \omega_y) \cdot h_{profile}(z)$$

In the literature, essentially the following methods of reconstruction in tomosynthesis are found:

Simple back-projection: [D. G. Grant, TOMOSYNTHESIS: A Three-Dimensional Radiographic Imaging Technique, IEEE Trans. on Biomed. Eng. 19 (1972), 20–28]: As in the classical slice method, by simple summation of the projection images an uncorrected reconstruction image is obtained. The method is rapid, simple and robust, but yields poor image results. Simple heuristic 2D filterings of the reconstructed tomograms [R. A. J. Groenhuis, R. L. Webber and U. E. Ruttimann, Computerized Tomosynthesis of Dental Tissues, Oral Surg. 56 (1983), 206–214] improve the image impression, but do not provide image material that can be reliably interpreted, and are thus not satisfactory.

Influencing of the recording geometry: By the selection of the sampling curve, such as e.g. spirals or threefold concentric circular scanning [U. E. Ruttimann, X. Qi and R. L. Webber, An Optimal Synthetic Aperture for Circular Tomosynthesis, Med. Phys. 16 (1989), 398–405], the point image function can be manipulated. The methods require a high mechanical outlay and are inflexible, since the image corrections are already determined with the measurement data. In addition, only slight image improvements have been achieved.

Iterative methods: [U. E. Ruttimann, R. A. J. Groenhuis and R. L. Webber, Restoration of Digital Multiplane Tomosynthesis by a Constrained Iteration Method, IEEE Trans. on Medical Imaging 3 (1984), 141–148]. With the aid of an iterative reconstruction, in principle the measurement process can be flexibly modeled and corrected by approximation. The iterative method attempts to invert the point image function. Since this is not possible, due to the incomplete scanning, secondary conditions must be introduced in order to guarantee the unambiguity of the solution. The methods achieve good image quality, but are not obvious and are difficult to use. In particular, the required introduction of secondary conditions can strongly falsify the image impression in an undesired manner. In addition, there are problems with the stability of the algorithms, and the computing time is prohibitive for a routine application.

Algebraic methods: For a set of tomograms, the point image function is set up slice-by-slice, which leads to a matrix formulation of the point image function. The exact inversion of the matrix is not possible, due to the incomplete scanning in the tomosynthesis. [J. T. Dobbins, Matrix Inversion Tomosynthesis Improvements in Longitudinal X-Ray Slice Imaging, U.S. Pat. No. 4,903,204, Feb. 20, 1990] falsely claims invertibility. This method, however, uses multiple subsequent corrections of the reconstruction images, which underlines the inadequacy of his approach. No publication of the image results, however, is available.

Reconstructive filtering methods: The present application is based on this principle. In the literature various approaches can be found, which can be classified on the basis of the space in which the filtering takes place. From the theoretical point of view, filtering in the 3D space of the object imaged or in the 2D space of the projection images are equivalent. The filters to be used can be transformed correspondingly.

Filtering in the 3D Fourier space of the imaged object [H. Matsuo, A. Iwata, I. Horiba and N. Suzumura, Three-Dimensional Image Reconstruction by Digital Tomosynthesis Using Inverse Filtering, IEEE Trans. on Medical Imaging 12 (1993), 307–313]: A filtering function is defined in the 3D Fourier space. A 3D reconstruction volume is obtained as a set of tomograms by simple back-projection. The reconstruction volume is transformed into the locus frequency space with the aid of the rapid Fourier transformation, and is filtered in that space and is back-transformed again. The method is essentially more computing-intensive than the filtering at the projection images, and is sensitive to discretization and to the size of the filtered reconstruction volume. From the theoretical point of view, [H. Matsuo, A. Iwata, I. Horiba and N. Suzumara, Three-Dimensional Image Reconstruction by Digital Tomosynthesis Using Inverse Filtering, IEEE Trans. on Medical Imaging 12 (1993), 307–313] have indeed calculated the correct 3D transmission function of the circular tomosynthesis function. The modification of the inverse filtering function which is selected mirrors the relations of a complete object scanning (computed tomography (CT) with surface detector and parallel beam approximation). The filtering function used corresponds to the generally known Shepp-Logan CT filter. The approach borrowed from CT does not do justice to the relations of tomosynthesis, and the image quality cannot be optimal.

Filtering in the 2D Fourier space of the projections (filtered back-projection): In the 2D Fourier space of the projections, a filtering is defined. Using fast Fourier transformation, the projection images are successively transformed into the locus frequency space, are filtered in that space, are back-transformed, and are subsequently calculated to form a reconstruction image by means of back-projection. The filtering can also be carried out in equivalent fashion in the locus region, by means of 2D convolution. The method is essentially faster than the 3D filtering, and has no artificial instabilities due to method parameters. The present invention likewise belongs to the class of filtered back-projections. From the literature, only ectomography [P. Edholm, G. Graniund, H. Knutsson and C. Petersson, Ectomography—A New Radiographic Method for Reproducing a Selected Slice by Varying Thickness, Acta Radiologica 21 (1980), 433–442] is known as a representative. In ectomography, however, the 2D filtering function is set up only empirically. The filters cannot be designed purposely for a particular optimization task, and an image manipulation, and thus a high image quality, is thus not achieved.

SUMMARY OF THE INVENTION

An object of the present invention is to provide a method for image reconstruction in which the image quality of the reconstruction image can be manipulated, and is improved in relation to the prior art.

The present invention provides the use of 2D filters in the filtered back-projection of the tomosynthesis for the production of the reconstruction image. On the basis of an analysis of the 3D transmission function, a filtering function is produced and is applied in the computing means for the reconstruction of the image. The entire procedure is divided into seven steps:

1. Calculation of a 3D transmission function $H_{proj}(\omega_x,\omega_y,\omega_z)$ from the recording geometry for the individual projection image recording, and the back-projection of the individual projection images into the 3D reconstruction image volume,
2. Approximate inversion of the 3D transmission function $H_{proj}(\omega_x,\omega_y,\omega_z)$ for the determination of an inversion function $H_{inv}(\omega_x,\omega_y,\omega_z)$,
3. Production of a 3D filtering function $H_{opt}(\omega_x,\omega_y,\omega_z)$ dependent on one or more desired image characteristics of the reconstruction image,
4. Determination of a resulting 3D filtering function $H_{filter}(\omega_x,\omega_y,\omega_z)$ by multiplication of the 3D filtering function $H_{opt}(\omega_x,\omega_y,\omega_z)$ and the inversion function $H_{inv}(\omega_x,\omega_y,\omega_z)$,
5. Determination of a 2D filtering function $H^{2D}_{filter,\phi}(\omega_u,\omega_v)$ from the resulting 3D filtering function $H_{filter}(\omega_x,\omega_y,\omega_z)$, by coordinate transformation of the 3D object space into the 2D projection image space of the respective individual projection images, at the projection angle $\phi$, after which the reconstruction of the image takes place in the computing means, with the following steps:

6. Application of the 2D filtering function $H^{2D}_{filter,\phi}(\omega_u,\omega_v)$ to the associated individual projection image data,
7. Production of the reconstruction image by back-projection of the individual projection image data, filtered according to 6., into the 3D reconstruction image volume.

The overall 3D transmission function thus results from the product of the individual components:

$$H(\omega_x, \omega_y, \omega_z) = \underbrace{H_{opt}(\omega_x, \omega_y, \omega_z) \cdot H_{inv}(\omega_x, \omega_y, \omega_z)}_{\text{3D filtering function to be applied } H_{filter}(\omega_x,\omega_y,\omega_z)} \cdot H_{proj}(\omega_x, \omega_y, \omega_z)$$

The object of the invention is also achieved in a procedure divided into six steps:

1. calculation of a 3D transmission function $H_{proj}(\omega_x,\omega_y,\omega_z)$ from the recording geometry for the individual projection image recordings, and back-projection of the individual projection images into the 3D reconstruction image volume, 2. Approximate inversion of the 3D transmission function $H_{proj}(\omega_x,\omega_y,\omega_z)$ for the determination of an inversion function $H_{inv}(\omega_x,\omega_y,\omega_z)$,
3. Determination of a 3D filtering function $H_{opt}(\omega_x,\omega_y,\omega_z)$ dependent on one or more desired image characteristics of the reconstruction image,
4. Determination of a resulting 3D filtering function $H_{filter}(\omega_x,\omega_y,\omega_z)$ by multiplication of the 3D filtering function $H_{opt}(\omega_x,\omega_y,\omega_z)$ and the inversion function $H_{inv}(\omega_x,\omega_y,\omega_z)$, after which the reconstruction of the image takes place in the computing means with the following steps:
5. Production of the reconstruction image by back-projection of the individual projection image data into the 3D reconstruction image volume,
6. Application of the resulting 3D filtering function $H_{filter}(\omega_x,\omega_y,\omega_z)$ to the reconstruction image for the filtering thereof.

Here, the reconstruction image itself is filtered, after its production, with the resulting 3D filtering function, in contrast to the solution previously described, in which the individual projection images are already filtered before the back-projection. Both methods have in common the application of the 3D filtering function according to the desired image characteristics, so that the reconstruction image shows the desired image characteristics.

The invention is suitable for all radiological applications, such as imagings of the skull, of the skeletal system and of the inner organs, as well as for applications in nuclear medicine with specific collimators.

DESCRIPTION OF THE PREFERRED EMBODIMENTS

Figure 1:
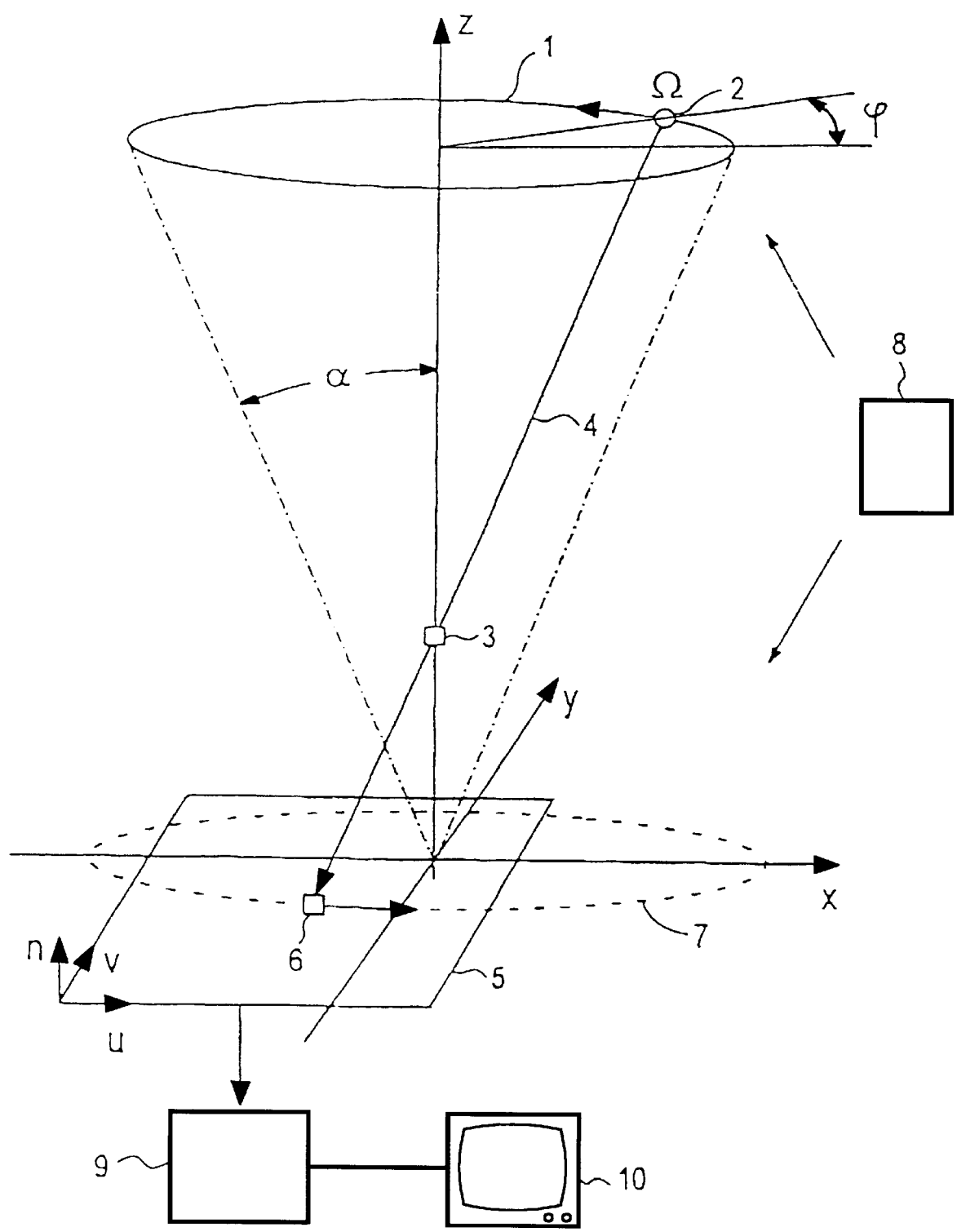
FIG. 1 shows a schematic representation of an inventive apparatus for illustrating the data recording process, given e.g. a circular scanning.

FIG. 1 shows a circle 1 on which an X-ray focus 2 revolves. An object 3 is imaged (image 6) on a detector 5 by an X-ray beam 4. The image 6 describes a circle 7. The detector 5 can, for example, be formed by a matrix of semiconductor detector elements whose output signals correspond to the respectively received beam intensity and are supplied to an image computer 9.

Concerning the above steps 1 to 5 in the first version of the invention, or the above steps 1 to 4 of the second version, the following is noted:

Concerning 1

Figure 2:
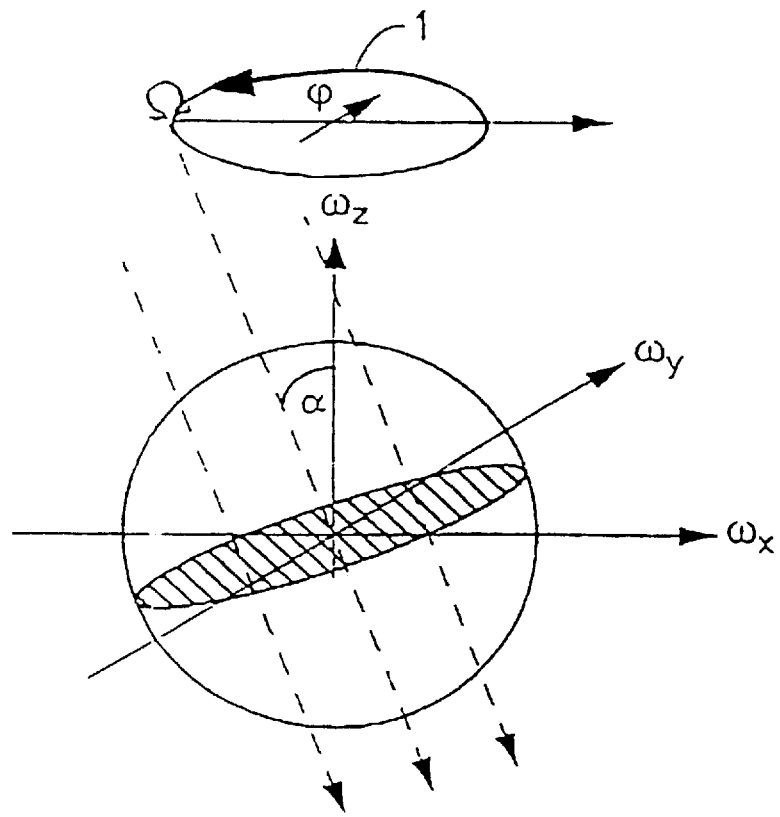
FIGS. 2 and 3 respectively show two representations for the explanation of the Fourier slice theorem, which is essential for the invention, given e.g. circular scanning.
Figure 3:
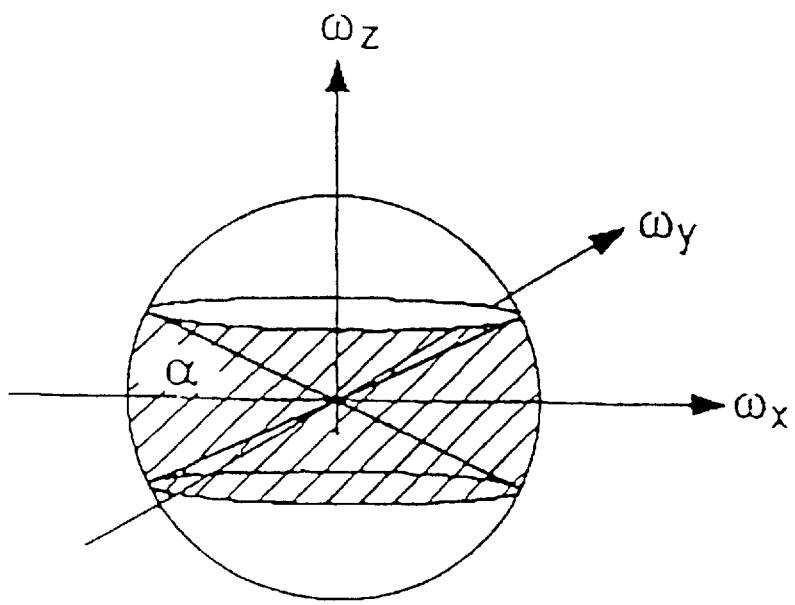

Calculation of the MTF of the Data Recording and Back-projection:

For the circular scanning, the 3D transmission function is calculated in cylindrical coordinates as $$H_{proj}(\omega_\rho, \omega_\varphi, \omega_z) = \frac{2}{\sin\alpha \cdot \sqrt{\omega_\rho^2 - \omega_z^2 \cdot \cot^2\alpha}}$$

in the scanned region $\omega_z \leq \omega_\rho \cdot \tan\alpha$,
or as 0 otherwise,
with $\omega_\rho$ being the cylindrically radial locus frequency and $\omega_z$ being the locus frequency in the parallel direction to the axis of rotation of the X-ray focus. Naturally, outside the scanned region the imaging process does not supply any image contributions. The boundaries of the scanned region result directly from the Fourier slice theorem (see FIGS. 2 and 3). FIG. 2 shows the projection of an object at a tomosynthesis angle $\alpha$ and a projection angle $\phi$, which corresponds in the 3D Fourier space to a scanning of the object on a plane perpendicular to the direction of radiation. The scanned plane is hatched. From FIG. 3 it follows that an overall circular recording cycle scans the object incompletely. The region of a double sphere in the $\omega_z$ direction is missing. The scanned region is hatched.

Concerning 2

Approximate Inversion of the 3D Transmission Function:

In the next step, the weightings of the 3D transmission function are to be compensated. An inversion of the MTF is however possible only where it does not vanish. In the case of circular scanning, the transmission function can be inverted completely within the scanned region.

$$H_{inv}(\omega_x, \omega_y, \omega_z) = \begin{matrix} 1 & \text{in the scanned region} \\ 0 & \text{otherwise} \end{matrix}$$

Explicitly, in Cylindrical Radical Coordinates this is:

$$H_{inv}(\omega_\rho, \omega_\varphi, \omega_z) = \frac{\sin\alpha}{2} \cdot \sqrt{\omega_\rho^2 - \omega_z^2 \cdot \cot^2\alpha}$$

In the scanned region $\omega_z \leq \omega_\rho \cdot \tan\alpha$ and =0 otherwise Concerning 3

Design of a 3D filtering According to a Posed Optimization Task.

After compensation of the weigthing of the 3D transmission function, the imaging is optimized with an additional 3D filter. Ideally, the filtering has the following aims:
  Formation of a homogenous slice profile.
  Spectral image manipulation for matching the image quality to the object characteristics that are of interest.
  Damping of high-frequency image portions that mostly contribute only to the noise. In particular at the Nyquist boundary, the spectrum should be filtered to zero.

Due to the incomplete scanning in the tomosynthesis, the above goals cannot be achieved without limitations. The formation of a homogenous (i.e. frequency-independent) slice profile is exactly possible only for high-pass-filtered tomograms. If, in contrast, one is interested in an equal weighting (equilibrium) of the lower locus frequencies as well, this always leads to a strong feed-through of artefacts. The compromises are to be accepted depends on the objects to be imaged and the requirements of the imaging. Some approach strategies are discussed below. Independent of the posed optimization task, within the scanned region the 3D filtering function should separate formally into a portion of the spectral image content $H_{spectrum}((\omega_x,\omega_y))$ and a portion $H_{profile}(\omega_z)$ that defines the slice profile: $H_{opt}(\omega_x,\omega_y) = H_{spectrum}(\omega_x,\omega_y) \cdot H_{profile}(\omega_z)$ in the scanned region, and =0 otherwise.

The separation is. only formal, because the two portions are implicitly combined with one another via the scan boundaries.

In order to illustrate the advantages of this approach, the 2D slice transmission function $h(\omega_x,\omega_y|z)$ is calculated:

$$h(\omega_x,\omega_y|z) = F_z^{-1} H(\omega_x, \omega_y, \omega_z) = H_{spectrum}(\omega_x,\omega_y) \cdot F_z^{-1} H_{profile}(\omega_z)$$

Due to the limited scanning region, $H_{profile}(\omega_z)$ is implicitly dependent on $\omega_x$ and $\omega_y$. Since the portion $H_{profile}(\omega_z)$ is supposed to define the slice profile, we can assume in general that $H_{profile}(\omega_z)$ is a band-limited function:

$$H_{profile}(\omega_z) = 0 \text{ for } |\omega_z| > \omega_{z,max}$$

$H_{profile}(\omega_z)$ becomes independent of $\omega_x$, $\omega_y$ when the carrier of $H_{profile}(\omega_z)$ is located completely in the scanning region; for the circular region this is (see FIG. 4) $\omega_\rho \cdot \tan \alpha > \omega_{z,max}$.

It is thus useful to divide the scanning region into two zones:

complete scanning, if the carrier of $H_{profile}(\omega_z)$ is located completely in the scanning region incomplete scanning, if the profile function $H_{profile}(\omega_z)$ is cut off by the scanning edges.

The division into complete and incomplete scanning depends on the specifically selected profile function $H_{profile}(\omega_z)$.

For the slice transmission function $h(\omega_x,\omega_y|z)$, two cases thus must be distinguished:

$h(\omega_x,\omega_y|z) = H_{spectrum}(\omega_x, \omega_y) \cdot h_{profile}(z)$ given complete scanning $h(\omega_x,\omega_y|z) = H_{spectrum}(\omega_x, \omega_y) \cdot \tilde{h}_{profile}(z|\omega_x,\omega_y)$ given incomplete scanning In the example of circular scanning, it can be seen that for high locus frequencies $\omega_\rho$ the slice transmission function $h(\omega_x,\omega_y|z)$ separates completely into a portion $H_{spectrum}(\omega_\rho)$, which determines the spectral content of the tomograms, and a portion $h_{profile}(z)$ that defines the slice profile. For small locus frequencies $\omega_\rho$, the slice profile is dependent on the locus frequency up shown in the tomogram. A locus-frequency-dependent slice thickness $\tilde{h}_{profile}(z|\omega_\rho)$ is typical for the incomplete scanning in tomosynthesis. The region of a defined (frequency-independent) slice profile depends on the tomosynthesis angle $\alpha$ and on the width ($\omega_{z,max}$ of the slice profile. For large tomosynthesis angles and thick slices, the filtered back-projection produces constant slice thickness over broad parts of the locus frequency spectrum.

Concerning 4. (According to the First Version of the Method)

The resulting filtering function $H_{filter}(\omega_x, \omega_y, \omega_z)$ results from the product $$H_{filter}(\omega_x,\omega_y,\omega_z) = H_{opt}(\omega_x,\omega_y, \omega_z) \cdot H_{profile}(\omega_x,\omega_y,\omega_z)$$

with $$H_{filter}(\omega_x,\omega_y,\omega_z) = H_{spectrum}(\omega_x, \omega_y,\omega_z) \cdot H_{profile}(\omega_x,\omega_y,\omega_z)$$

Concerning 5. (According to the First Version of the Method)

Figure 5:
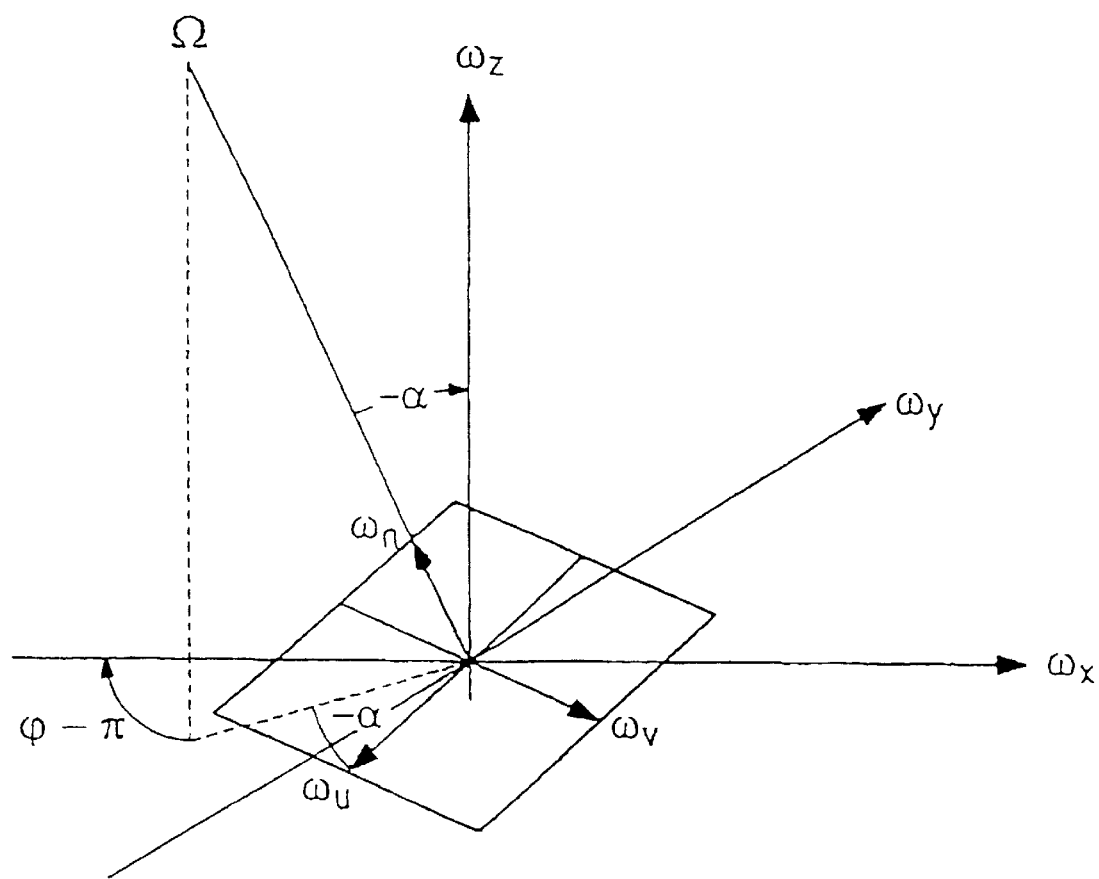
FIG. 5 shows the coordinate transformation with a rotating detector, given a circular scanning.

Transformation of the 3D Filtering Function into the 2D Space of the Projection Images:

The coordinate transformation depends on the scanning geometry, i.e. on the angle of incidence of the X-ray radiation, consisting of the tomosynthesis angle $\alpha$ and the projection angle $\phi$, and on the type of detector following. Subsequently, the coordinate transformation of the circular scanning is described. A number of variants of the detector following are conceivable; as examples, two of them are discussed, but other motions are possible.

a) Rotating Detector:

The Fourier slice theorem (see FIGS. 2 and 3) indicates which Fourier data were scanned in the 3D object space by means of projection onto a 2D detector. With the same theorem, the 3D filtering functions can also be transmitted from the 3D image space with the coordinates ($\omega_x$, $\omega_y$, $\omega_z$) back into the 2D projection image with the detector coordinates ($\omega_x$, $\omega_y$, $\omega_z$) with components $\omega_u$ perpendicular to the tangent of the scanning curve, $\omega_v$ parallel to the tangent of the scanning curve, and $\omega_n$ in the direction of the normal vector ($\omega_n=0$). For a detector that is rotated synchronously along with the X-ray focus, the detector coordinates transform to (see FIG. 5):

$$\begin{pmatrix} \omega_x \\ \omega_y \\ \omega_z \end{pmatrix} = \underline{D}_3(-\varphi) \cdot \underline{D}_2(-\alpha) \cdot \begin{pmatrix} \omega_u \\ \omega_v \\ \omega_n \end{pmatrix}$$

with tomosynthesis angle $\alpha$ and projection angle $\phi$. The rotation matrix $D_2$ describes a rotation around the 2-axis $$\underline{D}_2(\gamma) = \begin{pmatrix} \cos\gamma & 0 & -\sin\gamma \\ 0 & 1 & 0 \\ \sin\gamma & 0 & \cos\gamma \end{pmatrix}$$

the rotation matrix $D_3$ describes a rotation around the 3-axis $$\underline{D}_3(\gamma) = \begin{pmatrix} \cos\gamma & \sin\gamma & 0 \\ -\sin\gamma & \cos\gamma & 0 \\ 0 & 0 & 1 \end{pmatrix}$$

The resulting transformation is explicitly written:

$$\begin{pmatrix} \omega_x \\ \omega_y \\ \omega_z \end{pmatrix} = \begin{pmatrix} \omega_u \cdot \cos\alpha \cdot \cos\varphi - \omega_v \cdot \sin\varphi \\ \omega_u \cdot \cos\alpha \cdot \sin\varphi + \omega_v \cdot \cos\varphi \\ -\omega_u \cdot \sin\alpha \end{pmatrix}$$

With this transformation, the 3D filtering functions can be reformulated into 2D filters in the space of the projection images. The inverse $H_{inv}$ of the 3D transmission function of the circular scanning is equal to $$H_{inv}(\omega_u, \omega_v) = \frac{\sin\alpha}{2} \cdot |\omega_v|$$

The weighting of the 3D transmission function is compensated by means of a ramp filter parallel to the tangent of the scanning curve. The formally separating components of the additional 3D filtering function $H_{filter}$ transform to $$H_{spectrum}(\omega_\rho) \to H_{spectrum}(\sqrt{\omega_u^2 \cos^2\alpha + \omega_v^2})$$

$$H_{profile}(\omega_z) \to H_{profile}(-\omega_u \cdot \sin\alpha)$$

The components of the 3D filtering function no longer separate in the 2D Fourier space of the projection images.

b) Detector with Fixed Orientation:

In this detector, the transformation equation expands by a rotation about the 3-axis $$\begin{pmatrix} \omega_x \\ \omega_y \\ \omega_z \end{pmatrix} = \underbrace{D_3(-\varphi) \cdot D_2(-\alpha) \cdot D_3(\varphi)}_{\text{rotated filter}} \cdot \begin{pmatrix} \omega_u \\ \omega_v \\ \omega_n \end{pmatrix}$$

The 2D filter of the rotating detector can be taken over, but however must be rotated before its application by the projection angle $\varphi$.

Concerning 6. (According to the First Version of the Method)

The individual projection image data consist of a set of two-dimensional projection images $p_\varphi(u, v)$, of which each was recorded at a projection angle $\varphi$.

For each projection angle $\varphi$, the associated projection image $p_\varphi(u, v)$ is filtered, using the corresponding 2D filtering function $H^{2D}_{filter,\varphi}(\omega_u, \omega_v)$—there for; and to form a filtered projection image $\tilde{p}_\varphi(u,v)$. This can be carried out in the following manner:

Filtering in the spatial domain by convolution of the projection image $p_\varphi(u, v)$ with the 2D filtering function $h^{2D}_{filter,\varphi}(u,v)$ $$\tilde{p}_\varphi(u, v) * h^{2D}_{filter,\varphi}(u,v) = \int\int p_\varphi(u', v') \cdot h^{2D}_{filter,\varphi}(u'-u, v'-v) du' dv'$$

The 2D filtering function $h^{2D}_{filter,\varphi}(u,v)$ of the locus space can be calculated by means of Fourier back-transformation $F^{-1}$ of the 2D filtering function $H^{2D}_{filter,\varphi}(\omega_u, \omega_v)$ of the locus frequency space $$h_{filter,\varphi}^{2D}(u, v) = F_u^{-1} F_v^{-1} H_{filter,\varphi}^{2D}(\omega_u, \omega_v)$$

The calculation of the filtering function $h^{2Dfilter,\varphi}(u,v)$ need be carried out only once, and the filtering function can be stored for later applications.

Filtering in the locus frequency space by means of multiplication of the Fourier-transformed projection image $P_\varphi(\omega_u, \omega_v)$ with the 2D filtering function $H^{2Dfilter}(\omega_u, \omega_v)$ and subsequent Fourier back-transformation of the filtered projection image $$\tilde{P}_\varphi(\omega_u, \omega_v)$$

Fourier transformation:

$$P_\varphi(\omega_u, \omega_v) = F_v F_u p_\varphi(u, v)$$

Filtering:

$$\tilde{P}_\varphi(\omega_u, \omega_v) = H^{2D}_{filter,\varphi}(\omega_u, \omega_v) \cdot P_\varphi(\omega_u, \omega_v)$$

Fourier back-transformation:

$$\tilde{p}_\varphi(u,v) = F_u^{-1} F_v^{-1} \tilde{P}_\varphi(\omega_u, \omega_v)$$

Concerning 7. (According to the First Version of the Method)

The 3D reconstruction image $g(x,y,z)$ is calculated by back-projection $B_\varphi$ of the filtered projection images $\tilde{p}_\varphi(u,v)$ $$g(x, y, z) = \sum_\varphi B_\varphi \tilde{p}_\varphi(u, v)$$

For the back-projection, generally known standard methods can be used.

Concerning 5. (According to the Second Version of the Method)

The individual projection image data consist of a set of two-dimensional projection images $p_\varphi(u,v)$, of which each was recorded at a projection angle $\varphi$.

An unfiltered 3D reconstruction image $g_{unfiltered}(x,y,z)$ is calculated by back-projection $B_\varphi$ of the projection images $p_\varphi(u,v)$ $$g_{unfiltered}(x, y, z) = \sum_\varphi B_\varphi p_\varphi(u, v)$$

For the back-projection, generally known standard methods can be used.

Concerning 6 (According to the Second Version of the Method)

The unfiltered 3D reconstruction image $g_{unfiltered}(x,y,z)$ is filtered with the 3D filtering function $H_{filter}(\omega_x, \omega_y, \omega_z)$. This can be carried out in the following manner:

Filtering in the locus space by convolution of the unfiltered 3D reconstruction image $g_{unfiltered}(x,y,z)$ with the 3D filtering function $h_{filter}(x,y,z)$ $$g(x,y,z) = g_{unfiltered}(x,y,z) * h_{filter}(x,y,z) =$$

$$= \int\int\int g_{unfiltered}(x',y',z') \cdot h_{filter}(x'-x, y'-y, z'-z) dx' dy' dz'$$

The 3D filtering function $h_{filter}(x,y,z)$ of the locus space can be calculated by Fourier back-transformation $F^{-1}$ of the 3D filtering function $H_{filter}(\omega_x, \omega_y, \omega_z)$ of the locus frequency space $$h_{filter}(x,y,z) = F_x^{-1} F_y^{-1} F_z^{-1} H_{filter}(\omega_x, \omega_y, \omega_z)$$

The calculation of the filtering function $h_{filter}(x,y,z)$ need be carried out only once, and the filtering function can be stored for later applications.

Filtering in the locus frequency space by multiplication of the Fourier-transformed, unfiltered 3D reconstruction image $G_{unfiltered}(x,y,z)$ with the 3D filtering function $H_{filter}(\omega_x, \omega_y, \omega_z)$ and subsequent Fourier back-transformation of the filtered projection image $G(\omega_x, \omega_y, \omega_z)$ Fourier transformation $$G_{unfiltered}(\omega_x, \omega_y, \omega_z) = F_z F_y F_x g_{unfiltered}(x,y,z)$$

Filtering:

$$G(\omega_x, \omega_y, \omega_z) = H_{filter}(\omega_x, \omega_y, \omega_z) \cdot G_{unfiltered}(\omega_x, \omega_y, \omega_z)$$

Fourier back-transformation:

$$g(x, y, z) = F_x^{-1} F_y^{-1} F_z^{-1} G(\omega_x, \omega_y, \omega_z)$$

Filtering Strategies:

In the following, possible strategies for 3D filtering are presented. As shown above, which filtering appears suitable depends on the optimization criteria.

Figure 4:
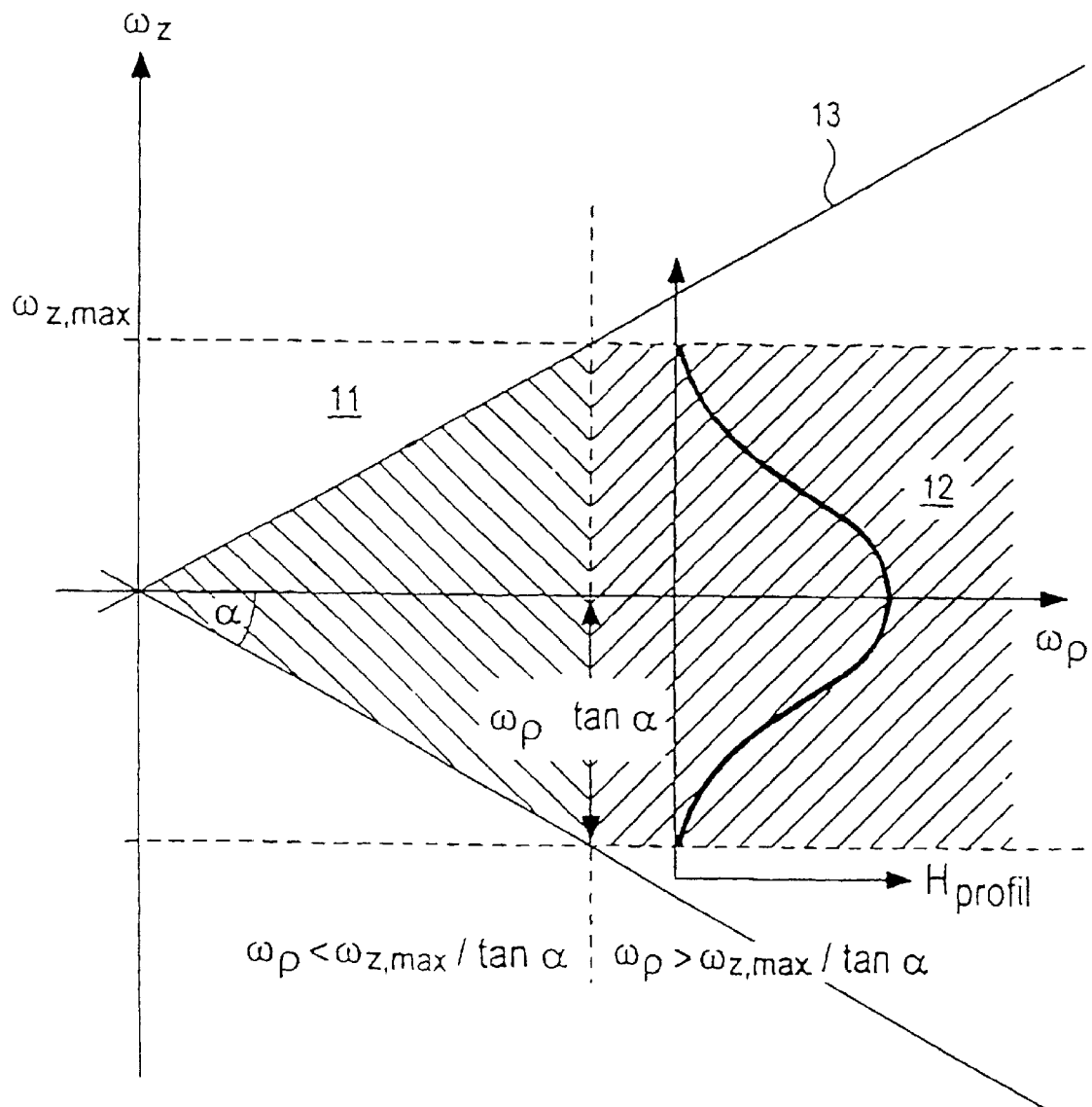
FIG. 4 shows a representation for the illustration of the complete and incomplete scanning regions in the locus frequency space for a given slice profile function, given a circular scanning.

Exact Reconstruction:

By an exact reconstruction is meant reconstruction with a slice profile independent of locus frequency. The slice information of an object is then present with a well-defined image spectrum. Above, in the calculation of the slice transmission function it was shown that a frequency-independent slice profile can form only when the carrier of $H_{filter}$ is located completely in the scanned region (FIG. 4). In FIG. 4, 11 designates the incomplete region with non-homogenous slice profile, 12 designates the complete region with homogenous slice profile, and 13 designates the scanning boundary. Since this is not fulfilled for lower locus frequencies, the relevant frequency spectrum must be limited in the radial direction by $H_{spectrum}(\omega_x,\omega_y)$ in such a way that there the scanned region completely contains the carrier of $H_{profile}(\omega_z)$. This means a bandpass filtering of the tomograms by means of $H_{spectrum}$. The lower boundary of the bandpass filtering depends on the tomosynthesis angle a and on the slice thickness or, respectively, on the boundary frequency $\omega_{z,max}$ of the filter component $H_{profile}$. For the circular scanning, this means $$H_{spectrum}(\omega_x, \omega_y) \equiv 0 \text{ for } (\omega_p) < \frac{W_{z'limit}}{\tan\alpha} \Rightarrow$$

$$h(\omega_x, \omega_y|z) = H_{spectrum}(\omega_x, \omega_y) \cdot h_{profile}(z)$$

The image portions in the incompletely scanned region are eliminated with the spectral function for the formation of a constant slice profile.

Toleration of the Frequency-dependent Slice Thickness:

If the blurring artefacts due to slice feed-through of low-locus-frequency image portions for the respective application are tolerable, the filter portions $H_{spectrum}$ for the manipulation of the spectral content of the tomograms and $H_{profile}$ for the approximate formation of a slice profile can be freely selected. However, it must always be taken into account that in the incompletely scanned region the spectral content of the tomograms also depends on the slice profile and on the size of the scanning region (FIG. 4).

In FIGS. 4, 6 and 7, 11 designates the incomplete region (non-homogenous slice profile), 12 designates the complete region (homogenous slice profile), and 13 designates the scanning boundary.

Suppression of the Portions with Frequency-dependent Slice Profile:

The spectral portion in the tomogram in the region of incomplete scanning with frequency-dependent slice profile is naturally suppressed by the reduced scanning region (FIG. 4). The damping is dependent on the distance z to the slice plane, the size of the scanned region and the curve of the slice profile function. For a slice profile function normalized in the completely scanned region, given z=0 the damping of the spectral portion is identical to the slice profile component of the slice transmission function (see above).

$$\tilde{h}_{profile}(z = 0|\omega_x, \omega_y) = \int_{-(\omega_x,\omega_y)\tan\alpha}^{+(\omega_x,\omega_y)\tan\alpha} H_{profile}(\omega_z) \cdot d\omega_z$$

If this natural suppression is not sufficient, it can be supported by an additional damping in the component $H_{spectrum}$ of the 3D filter, in order to obtain, by approximation, a reconstruction with a defined slice profile.

The image portions with locus-frequency-dependent slice profile in the incompletely scanned region are weighted less strongly with the special function.

Equal Weighting of the Low-frequency Image Portions:

As was just shown, the spectral portion of low-frequency locus frequencies is damped naturally. This is generally advantageous, because by this means the image artefacts due to poor depth resolution of low-frequency structures are reduced. If great importance is attached to the representation of low-frequency structures, the filter components $H_{spectrum}$ can be normalized by approximation with the integral of the filter component $H_{profile}$ in $\omega_z$ $$H_{spectrum}(\omega_x, \omega_y) \to \frac{H_{spectrum}(\omega_x, \omega_y)}{\tilde{h}_{profile}(z = 0|\omega_x, \omega_y)}$$

For object structures in the slice plane (z=0), this leads to an exact equal weighting of the low-frequency image portions; for structures outside the slice plane, an equal weighting can be achieved only approximately. The inherent damping of image portions in the incomplete region is compensated with the spectral function according to the above equation, so that an equal weighting of all image portions is achieved.

Figure 6:
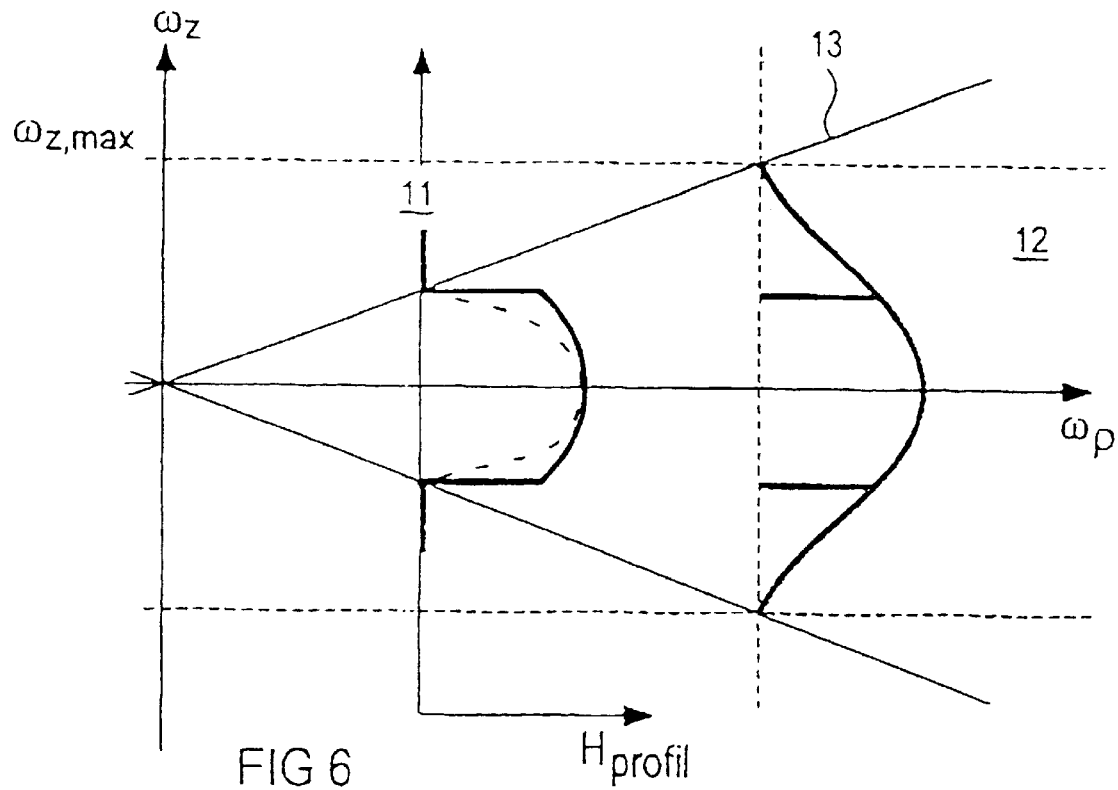
FIGS. 6 and 7 illustrate the smoothing of truncated slice profile functions.
Figure 7:
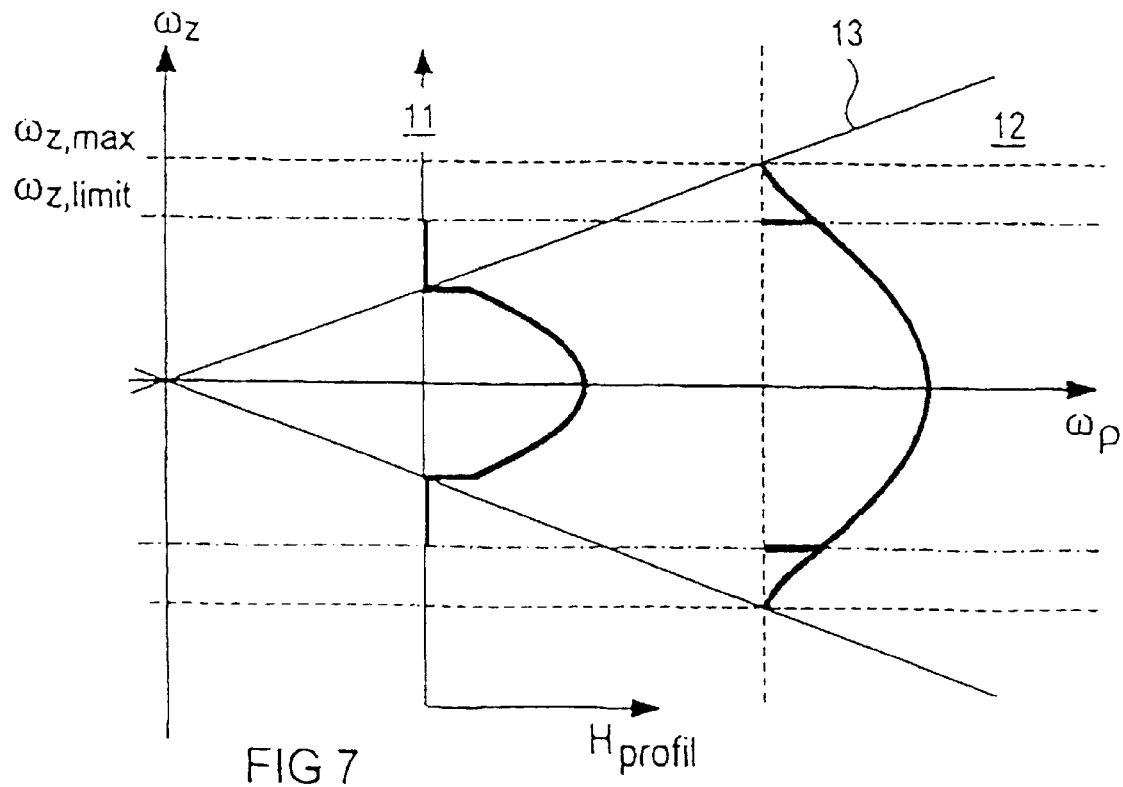

Reduction or avoidance of truncation edges of the filter component $H_{profile}$:

If the 3D transmission function H has high truncation edges in the $\omega_z$ direction, the slice profile develops an extensive oscillation characteristic. This has the consequence that after an apparent decaying out of the slice feed-through, new disturbing structures are built up in the tomogram from still further removed object slices. This oscillation characteristic in the slice profile can be avoided by means of a smooth, continuous transition of the 3D transmission function at the scanning boundaries, e.g. using the following approaches:

a) Smoothing of the truncation edges in the filter components $H_{profile}$ for the slice profile formation (FIGS. 6 and 7)

By means of a purposive smoothing of the filter components $H_{profile}(\omega_z)$ at the scanning boundaries, an abrupt truncation of the 3D transmission function can be avoided (FIG. 6). The smoothing leaves the slice thickness and the frequency dependence of the slice profile almost unaffected, and purposively eliminates the extensive oscillation characteristic of the slice profile. A smoothing can take place by multiplication of the filter component $H_{profile}(\omega_z)$ with a smoothed window function, in particular in the form of a step function, that is equal to one within the scanning region and at the boundaries falls continuously and differentiably to zero. For each radial frequency, the window function must be adapted to the current width of the scanning region. An alternative smoothing possibility is the convolution of the filter component $H_{profile}(\omega_z)$ with a smoothed core. The convolution has the disadvantage that it also smooths the slice profile in the interior of the scanning region.

b) Scaling of the filter component $H_{profile}$ for the slice profile development:

By means of a simple scaling of the filter component $H_{profile}(\omega_z)$, a truncation edge can be reduced in height, or can even be avoided completely (see FIG. 7). For circular scanning, the scaling has for example the following form:

$$\omega_z \rightarrow \omega_z \cdot \min\left(1, \frac{\omega_{z,limit}}{(\omega_\rho) \cdot \tan\alpha}\right)$$

with $\omega_{z,limit} \leq \omega_{z,max}$

If the scanning boundary at $(\omega_\rho) \tan(\alpha)$ is below the determined boundary or limit $\omega_{z,limit}$, the filter component $H_{profile}$ is compressed at these locations in such a way that it truncated at the scan boundaries with the value $H_{profile}(\omega_{z,limit})$. If the scaling limit is set $\omega_{z,limit}=\omega_{z,max}$, the 3D filtering function disappears. at the scanning boundaries, and truncation edges are thus completely avoided. This filtering strategy eliminates the extensive oscillation characteristic of the slice profile, at the cost of an increased slice thickness. The degree of increase is frequency-dependent, and increases as the radial locus frequency decreases.

c) Combination of smoothing (a) (FIG. 6) and scaling (b) (FIG. 7).

Given a scaling of the filter components $H_{profile}(\omega_z)$ (method b) with a limit frequency $\omega_{z,limit} \leq \omega_{z,max}$ that is smaller than the band limitation of the filter component $H_{profile}(\omega_{z,limit})$, the break-off edge at the scanning boundary is only decreased, but not avoided. The remaining truncation edge can be smoothed using the methods from (a).

The invention provides, among other things, an analytical concept for the design of 2D filters for filtered back-projection in tomosynthesis. In the literature, only empirically found filters are proposed. The connection between 3D transmission function, slice profile, depth resolution, spectral image content and incomplete scanning is not discussed in the literature, or is only hinted at.

With the new design, it is possible to convert application-specific requirements on image quality in a purposive manner. If it should turn out that many characteristics of image quality can be realized only at the expense of others, this can be analyzed precisely in the design presented, and a suitable compromise can be found. With the analytical design, solutions to new problems can also be worked out easily. The design is applicable to any scanning geometry, e.g., here it has been formulated. for circular scanning, and further below for linear scanning. It is not important for the principle of the method which specific filtering functions are finally applied.

The method is easy to understand and is thus flexibly adaptable to the respective application. The reconstruction is relatively fast, and can supply image results on current computing equipment in real time. The method achieves a defined image quality that comprises notable improvements in relation to simple back-projection.

In the following, as an example the embodiment from the transmission tomography according to FIG. 1 is described in more detail. The filtering methods of this invention, however, can also be used in other imaging modalities.

The embodiment for transmission tomography with circular scanning (FIG. 1) consists of the following components: an X-ray source, means for displacing the X-ray source with the X-ray focus 2 on the circle 1 in a plane, means for fixing the object 3 to be examined, patient fixing in medical applications, digital planar detector 5 for the measurement of the penetrating X-ray radiation opposite the transirradiated object 3, and means for displacing the detector 5 on the circle 7 in a plane. It is advantageous to arrange the planes of movement of the X-ray source and the detector 5 in parallel. The displacement takes place by 180° phase-offset to that of the X-ray source.

A computer 8 is provided for controlling the displacement of the X-ray source and the detector 5, for controlling the radiation process for controlling the image recording by the detector 5 (synchronized with the X-ray source), for storing the recorded projection images, for the reconstructive recalculation of the projection images to form a set of tomograms by means of filtered back-projection (computer 9), for the visualization of the image results on a monitor 10, and for storing the tomograms.

For a standard recording, a filtering function is selected that consists of the following components:

a) approximate inverse of the transmission function of the data recording and back-projection in the 3D Fourier space of the object/volume image (in the scanned region $\omega_z \leq \omega_\rho \cdot \tan\alpha$)

$$H_{inv}(\omega_\rho, \omega_\varphi, \omega_z) = \frac{\sin\alpha}{2} \cdot \sqrt{\omega_\rho^2 - \omega_z^2 \cdot \cot^2\alpha}$$

in the 2D Fourier space of the projection image $$H_{inv}(\omega_u, \omega_v) = \frac{\sin\alpha}{2} \cdot |\omega_v|$$

b) Portion of the spectral image content in the 3D Fourier space of the object/volume image (in the scanned region $\omega_z \leq \omega_\rho \cdot \tan\alpha$)

$$H_{spectrum}(\omega_\rho) = \frac{2}{B_v \cdot \sin\alpha} \cdot \text{sinc}\left(\frac{1}{B_v} \cdot \omega_\rho\right)$$

for $\omega_\rho < \pi \cdot B_v$
and $=0$ otherwise in the 2D Fourier space of the projection image $$H_{spectrum}(\omega_u, \omega_v) = \frac{2}{B_v \cdot \sin\alpha} \cdot \text{sinc}\left(\frac{1}{B_v} \cdot \sqrt{\omega_v^2 + \omega_u^2 \cdot \cos^2\alpha}\right)$$

c) Slice profile function in the 3D Fourier space of the object/volume image (in the scanned region $\omega_z \leq \omega_\rho \cdot \tan\alpha$)

$$H_{profile}(\omega_z) = \frac{1}{2\pi \cdot B_u} \cdot \left(1 + \cos\frac{\omega_z}{B_u}\right)$$

for $\omega_z < \pi \cdot B_u$
and $=0$ otherwise in the 2D Fourier space of the projection image $$H_{profile}(\omega_u, \omega_v) = \frac{1}{2\pi \cdot B_u} \cdot \left(1 + \cos\left(\frac{\sin\alpha}{B_u} \cdot \omega_u\right)\right)$$

The inverse necessarily results from the scanning geometry. The portion of the spectral image content is selected so that low-locus-frequency image portions are damped only by the incomplete scanning. A so-called "von Hann" window serves as a slice profile function.

For each projection angle $\phi$, the associated projection image $p_\phi(u,v)$ is filtered using the corresponding 2D filtering function $H2D_{filter,\phi}(\omega u, \omega v)$. This is carried out by means of filtering in the locus frequency space by multiplication of the Fourier-transformed projection image with the 2D filtering function $H^{2D}_{filter,\phi}(\omega_u, \omega_v)$ and subsequent Fourier back-transformation of the filtered projection image. The 3D reconstruction image g(x,y,z) is calculated by back-projection of the filtered projection images. A generally known standard method for back-projection is used, e.g. a voxel-driven back-projector that determines for each voxel the corresponding filtered projection values, and increments the voxel value thereby.

The invention was described above in connection with an X-ray source having a focus 2 that moves on a circular path 1 on the one side and a surface detector 5, moved synchronously thereto, on the other side of the measurement region for the object 3. It is also possible to move the X-ray focus 2 on a path that deviates therefrom, e.g. on a linear path. As another alternative, the surface detector 5 can be stationary, given a corresponding construction.

Figure 8:
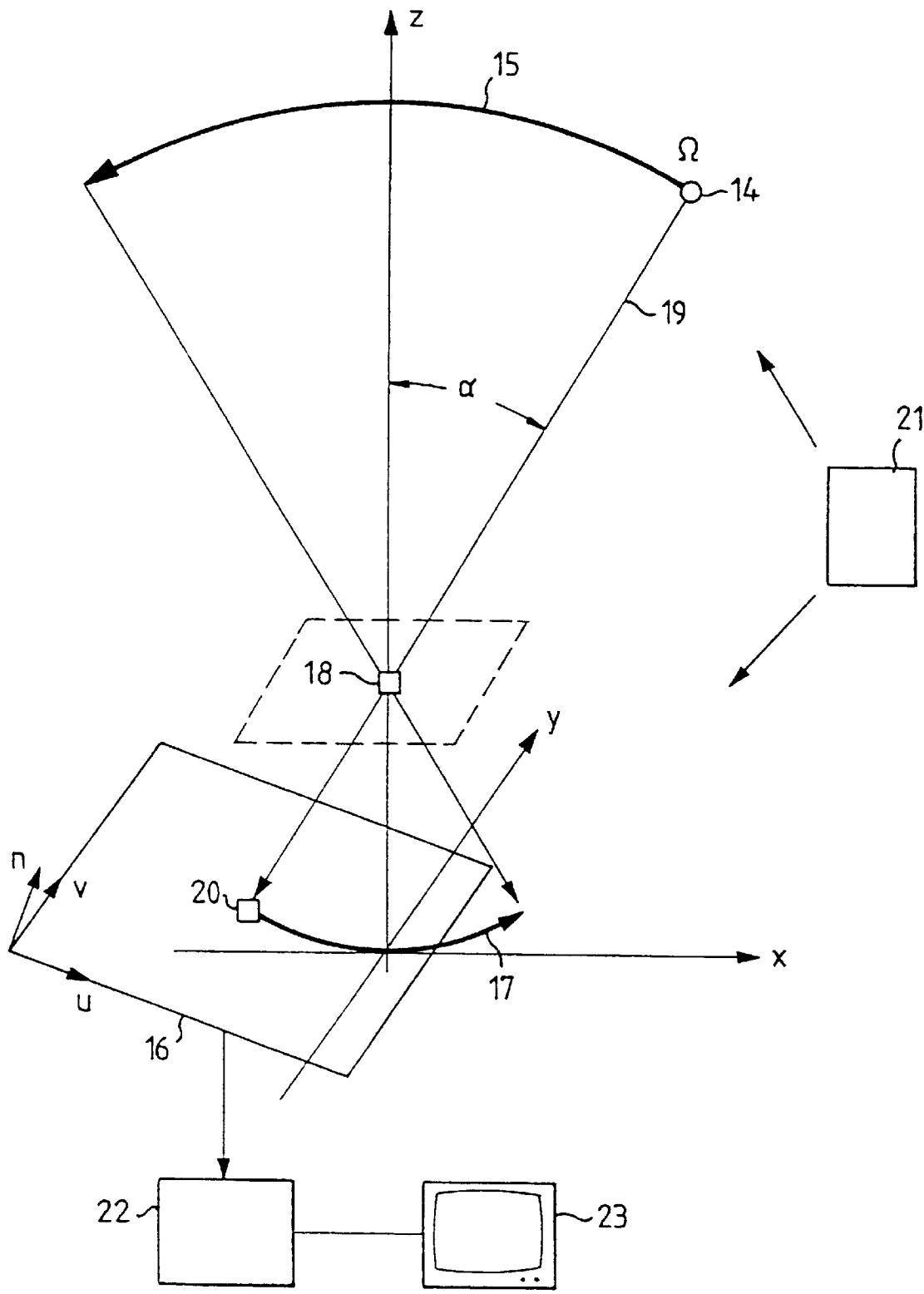
FIGS. 8 and 9 illustrate the data recording process of the linear scanning in a C-arm-like arrangement, with focus and detector moved along a circular path (FIG. 8), as well as in an arrangement similar to an X-ray table, with focus and detector moved along a straight line (FIG. 9).
Figure 9:
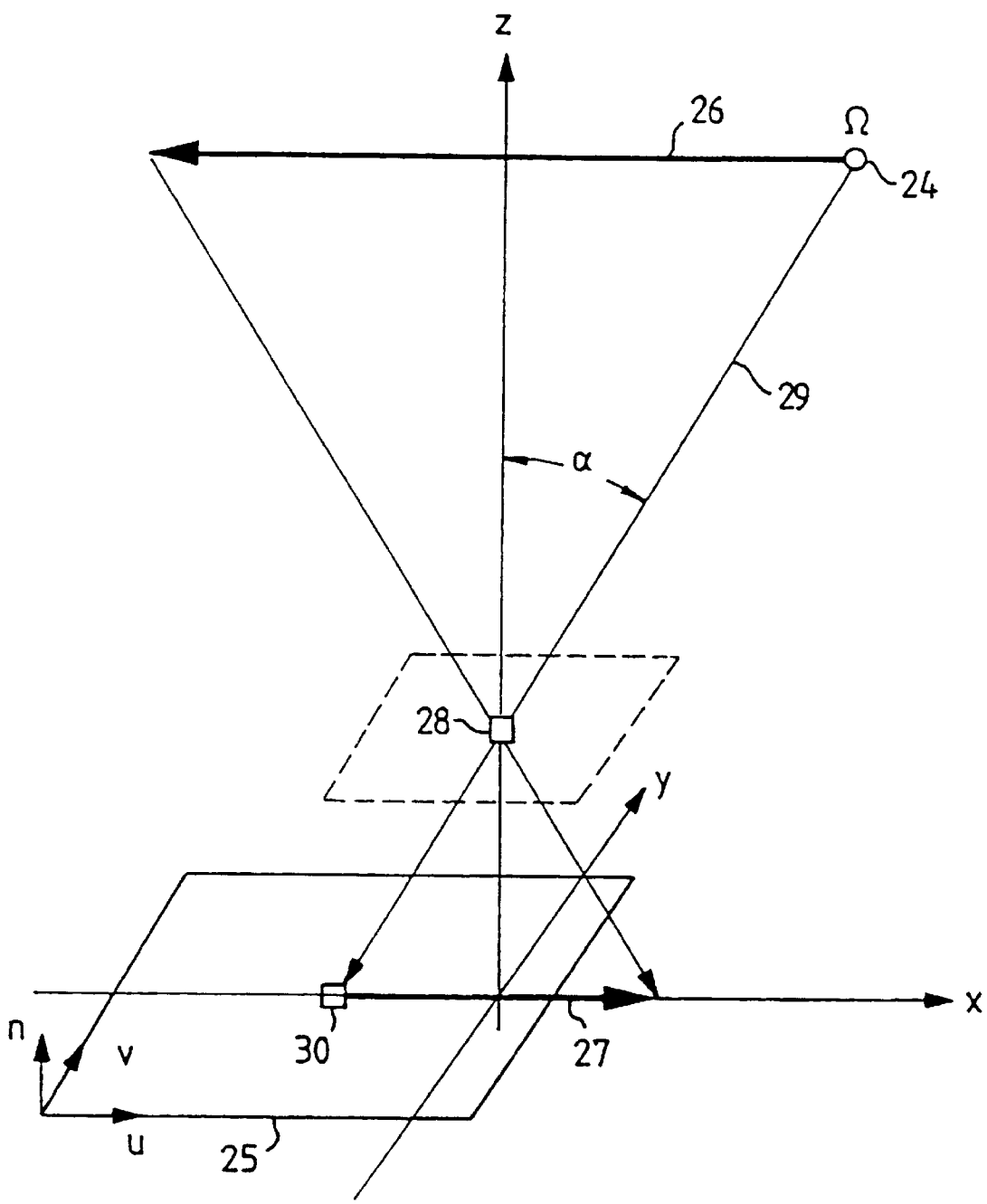

In the following, the reconstruction method is described specifically for linear scanning with various filters adapted to specific optimization tasks. In the context of linear scanning, two different scan geometries are possible, as specified in FIGS. 8 and 9. FIG. 8 shows the data recording process of linear scanning in a C-arm-like arrangement. Here the X-ray focus 14 is moved along a circular arc segment path 15, and the detector 16 is likewise moved along a circular arc segment path 17, but in the opposite direction. The object 18, located near the isocenter, is transirradiated with an X-ray beam 19, and an image 20 forms on the detector 16. The control of the motion of the X-ray focus 14 and of the detector 16 takes place by means of a computer 21. The signals emitted by the matrix detector 16 are supplied to an image computer 22 that emits the image produced to the monitor 23. In the modification according to FIG. 9, the X-ray focus 24 and the detector 25 are moved along two straight lines 26, 27, but here as well in the opposite direction. Here as well, after transirradiation of the object 28 with an X-ray beam 29 an image 30 results on the detector. Here as well, a computer (not shown) that controls the motion is used, as are an image computer and a corresponding output monitor. The scan geometry is not limited to that just specified; other variants are also conceivable.

In the following, the points 1 to 5 according to the first version of the method are explained in more detail for the special case of linear scanning, whereby the equations are numbered, due to the necessity of frequent reference.

Concerning 1.) Calculation of the MTF of the Data Recording and Back-projection

In the C-arm-like arrangement (FIG. 8), the X-ray focus and detector are moved on a circular arc segment in the xz plane, whereby at the vertex (middle projection) the tangents of the paths are directed parallel to the x axis. The detector is always oriented perpendicular to the incidence of the radiation. In the X-ray-table-like arrangement (FIG. 9), the X-ray focus and detector are moved on a straight line parallel to the x axis. The detector is always oriented parallel to the reconstruction slice plane. The scan geometry is not limited to that specified; other variants are also possible.

In addition to the scan arrangements discussed above, the types of scanning must still be distinguished: in equi-angle-distant scanning, the modification of the angle of incidence $\phi$ of the scan radiation is constant in time (constant angular speed). In equi-path-distant scanning, the radiation source moves at a speed that is constant in direction and magnitude. Equi-angle-distant scanning is typical for the C-arm-like arrangement, and equi-path-distant scanning is standardly used in X-ray-table-like arrangements. However, these allocations are not absolutely necessary. The 3D transmission function in the Fourier space is calculated in parallel beam approximation as:

equi-angle-distant scanning $$H_{proj}(\vec{\omega}) = \frac{1}{2 \cdot \alpha \cdot |\omega_x| \cdot \sqrt{1 + \left(\frac{\omega_z}{\omega_x}\right)^2}} \quad \text{(Eq. 1)}$$

in the scanned region $|\omega_z| \leq |\omega_x| \cdot \tan \alpha$ and $H_{proj}(\vec{W})=0$ otherwise.

equi-path-distant scanning $$H_{proj}(\vec{\omega}) = \frac{\sqrt{1 + \left(\frac{\omega_z}{\omega_x}\right)^2}}{2 \cdot \tan\alpha \cdot |\omega_x|} \quad \text{(Eq. 2)}$$

in the scanned region $|\omega_z| \leq |\omega_x| \cdot \tan \alpha$ and $H_{proj}(\vec{W})=0$ otherwise.

Figure 10:
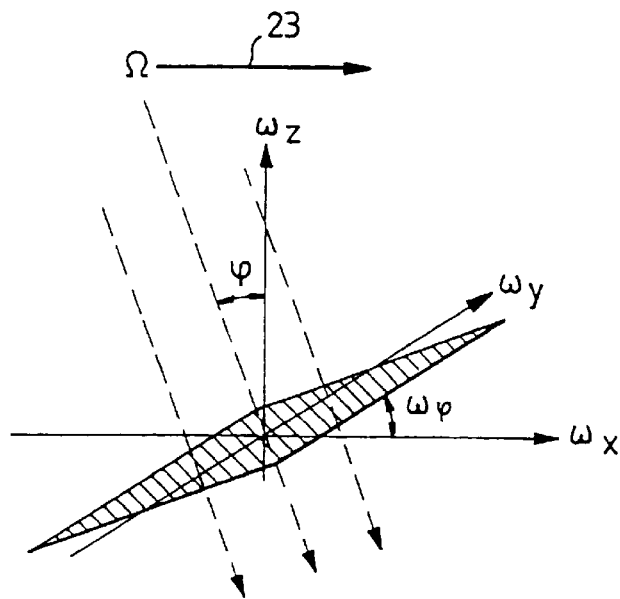
FIGS. 10 and 11 respectively show two representations for explanation of the Fourier slice theorem, for the illustration of the region scanned with a linear recording cycle.
Figure 11:
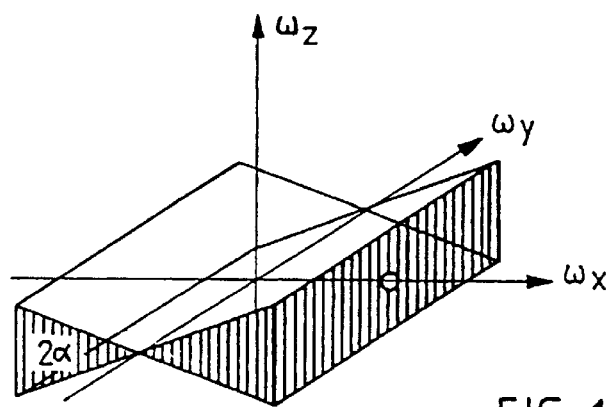

The boundaries of the scan region result directly from the Fourier slice theorem (see FIGS. 10 and 11). The projection of an object at an angle $\phi$ corresponds in the 3D Fourier space to a scanning of the object on a plane perpendicular to the direction of radiation (FIG. 10). An overall linear scan cycle scans the object incompletely. The scanned region here consists of a double V-formation, symmetrical in the xx direction, with an angle of opening $2\alpha$.

Approximation of small tomosynthesis angles

For small tomosynthesis angles $\alpha \ll 1$, there result the approximations $\alpha \approx \tan \alpha$, as well as $|\omega_z|/|\omega_x| \ll 1$. The transmission functions of the equi-angle-distant and equi-path-distant scanning thereby approximate a common expression.

$$H_{proj}(\vec{\omega}) = \frac{1}{2 \cdot \tan\alpha \cdot |\omega_x|} \quad \text{(Eq. 3)}$$

in the scanned region $|\omega_z| \leq |\omega_x| \cdot \tan \alpha$ and $H_{proj}(\vec{W})=0$ otherwise.

For larger tomosynthesis angles a as well, the above approximation is mostly sufficient, since the errors produced thereby are small as a rule in relation to the errors due to the incomplete scanning.

Concerning 2.) Approximate Inversion of the 3D Transmission Function

An inversion of the MTF is possible only where it is different from zero. In the case of linear tomosynthesis, the transmission function can be completely inverted within the scanned region. Explicitly, e.g. for the common expression of the equi-angle-distant and equi-path-distant scanning in the approximation of small tomosynthesis angles (Eq. 3)

$H_{inv}(\vec{\omega}) = 2 \tan \alpha \cdot |\omega_x|$ in the scanned region $|\omega_z| \leq |\omega_x| \cdot \tan \alpha$ and $$H_{inv}(\vec{\omega})=0 \text{ otherwise} \quad \text{(Eq. 4)}$$

Concerning 3.) Design of a 3D Filtering Function According to a Posed Optimization Task With the additional filtering function, the following aims can be pursued:

reduction of filter-caused overshootings by slow screening out of the contributions at the scan edge with a profile function $H_{profile}(\omega_x)$ in sub-areas, development of a homogenous slice profile by means of a profile function $H_{profile}(\omega_z)$ spectral image manipulation by means of a spectral function $H_{spectrum}(\omega_x,\omega_y)$ Independent of the posed optimization task, the 3D filtering function should separate formally inside the scanned region into the portions of the above profile and spectral function $$H_{opt}(\vec{\omega}) = H_{spectrum}(\omega_x, \omega_y) \cdot H_{profile}(\omega_z) \quad \text{in the scanned region} \quad \text{(Eq. 5)}$$
$$|\omega_z| \leq |\omega_x| \cdot \tan\alpha$$
$$H_{opt}(\vec{\omega}) = 0 \quad \text{otherwise}$$

The separation is only formal, since the two portions are implicitly connected with one another via the scan boundaries. The spectral function will not be discussed further here. Its optimization tasks and an embodiment have already been described above. Some approaches for the profile function are discussed further below.

Concerning 4.) Determination of a Resulting 3D Filtering Function

The resulting filtering function $H_{filter}(\omega_x,\omega_y,\omega_z)$ results from the product with $$H_{filter}(\omega_x,\omega_y,\omega_z) = H_{opt}(\omega_x,\omega_y,\omega_z) \cdot H_{inv}(\omega_x,\omega_y,\omega_z)$$

and $$H_{opt}(\omega_x,\omega_y,\omega_z) = H_{spectrum}(\omega_x,\omega_y,\omega_z) \cdot H_{profile}((\omega_x,\omega_y,\omega_z)$$

Figure 12:
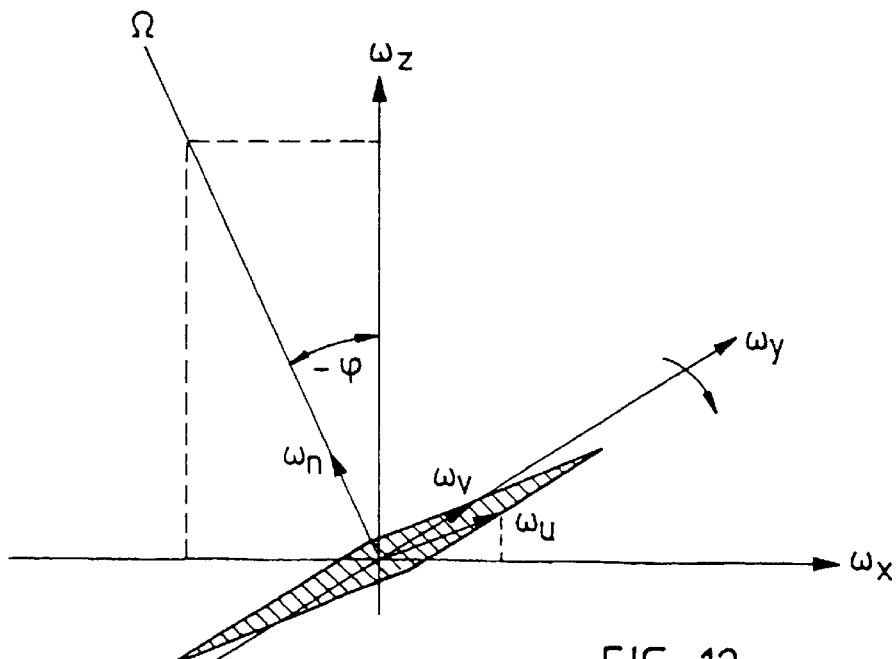
FIG. 12 shows the coordinate transformation for the conversion of the 3D coordinates of the object space into the 2D coordinates of the projection image, given linear scanning.

Concerning 5.) Transformation of the 3D Filtering Function into the 2D Space of the Projection Images With the aid of the Fourier slice theorem (FIG. 10), the 3D filtering function can be transmitted from the 3D image space with the coordinates $(\omega_x,\omega_y,\omega_z)$ into the 2D projection image with the detector coordinates $(\omega_u,\omega_v,\omega_n)$, with the components $\omega_u$ and $\omega_v$ being located in the detector plane, $\omega_u$ located parallel to the tangent of the scanning curve, $\omega_v$ located perpendicular thereto, and $\omega_n$ pointing in the direction of the normal vector of the detector plane (FIG. 12). Given a projection angle $\phi$, the transformation equation is $$\begin{pmatrix}\omega_x\\\omega_y\\\omega_z\end{pmatrix} = D_2(-\varphi) \cdot \begin{pmatrix}\omega_u\\\omega_v\\\omega_n\end{pmatrix} \quad \text{(Eq. 6)}$$

with the rotation matrix $D_2$ as specification of a rotation about the 2-axis $$D_2(\varphi) = \begin{pmatrix}\cos\varphi & 0 & -\sin\varphi\\ 0 & 1 & 0\\ \sin\varphi & 0 & \cos\varphi\end{pmatrix} \quad \text{(Eq. 7)}$$

In a C-arm-like arrangement with a sensor perpendicular to the direction of radiation, there results for the filtering function $$H^{2D}_{filter,\phi}(\omega_u,\omega_v) = H_{filter}(\omega_u \cdot \cos\phi, \omega_v - \omega_u \cdot \sin\phi) \quad \text{(Eq. 8)}$$

In an X-ray-table-like arrangement with a detector that is always located parallel to the reconstruction slice plane, a projection-angle-dependent scaling of the coordinate axes must be taken into account due to the oblique incidence of the radiation $$\omega_u \to \frac{\omega_u}{\cos\varphi} \text{ and } \omega_v \to \omega_v \quad \text{(Eq. 9)}$$

The 2D filtering function of the projections from Eq. 8 thus becomes:

$$\tilde{H}^{2D}_{filter,\varphi}(\omega_u, \omega_v) = H_{filter}(\omega_u, \omega_v - \omega_u \cdot \tan\varphi) \quad \text{(Eq. 10)}$$

Concerning steps 6 and 7, in the linear scanning nothing new results in relation to the general specification.

Of course, the linear scanning can also be handled with the second version of the method.

Approaches for the Profile Function

In the general specification of the invention, some filtering strategies were discussed independent of the respective scan curve. Of course, these can also be used for linear tomosynthesis. Here the discussion can be limited to approaches that are suitable specifically for linear scanning. A point of emphasis will be the reduction of filter-caused overshootings due to attenuation of the contributions at the scan edge.

(1) Filtering as Image Post-processing

With a constant profile function $H_{profile}(\omega_z)$ 1, the resulting 3D filtering function in the approximation of small tomosynthesis angles (Eq. 4) is independent of the z component of the locus frequency $$H_{filter} = H_{filter}(\omega_x, \omega_y) \quad \text{(Eq. 11)}$$

Thus, the filter can also be applied subsequently to the reconstruction image obtained by simple back-projection. Since the filtering function is the same in all tomograms, an efficient implementation, by approximation, of the 2D filter can be tried (e.g., formulation of a 2D filter kernel in the spatial domain with small core length).

The approach saves considerable computing time, but the image impression can be disturbed by strong overshootings. The non-constant, rectangular truncation at the scan edges can lead to an extensive sinc-shaped oscillation characteristic of the locus-frequency-dependent slice profile in the spatial domain.

(2) Formation of a Homogenous Slice Profile (in Subregions)

Figure 13:
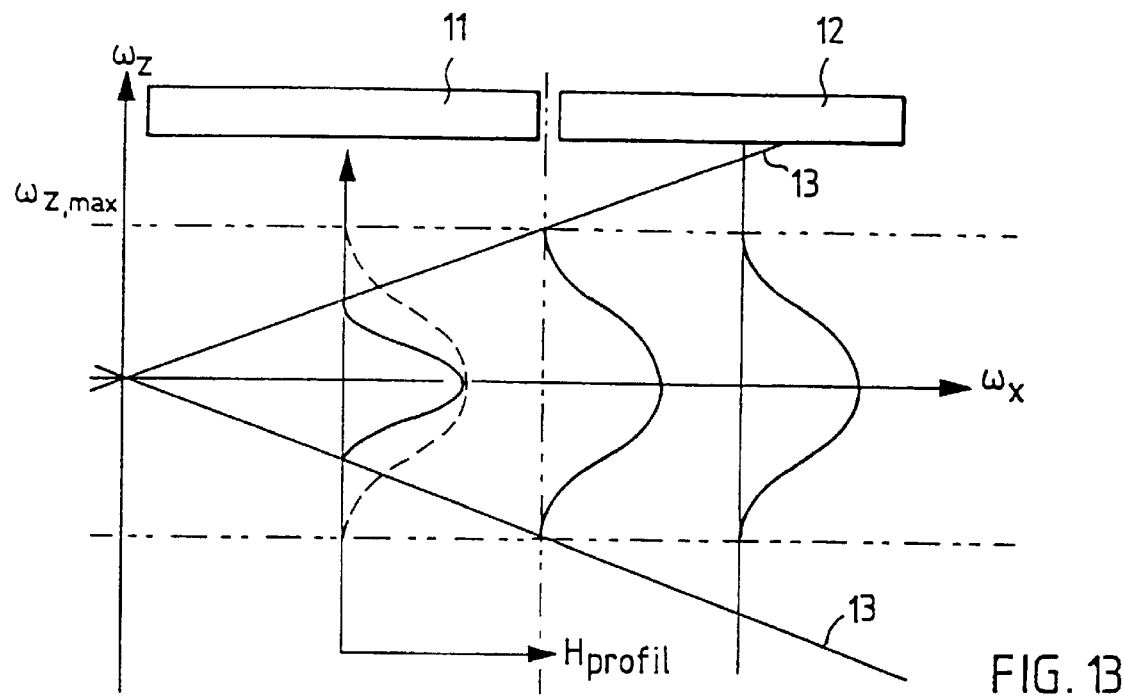
FIGS. 13 and 14 illustrate the smoothing of the truncation edges of a cut-off slice profile function by means of scaling in the region of incomplete scanning (FIG. 13) and over the entire scanning region (FIG. 14).
Figure 14:
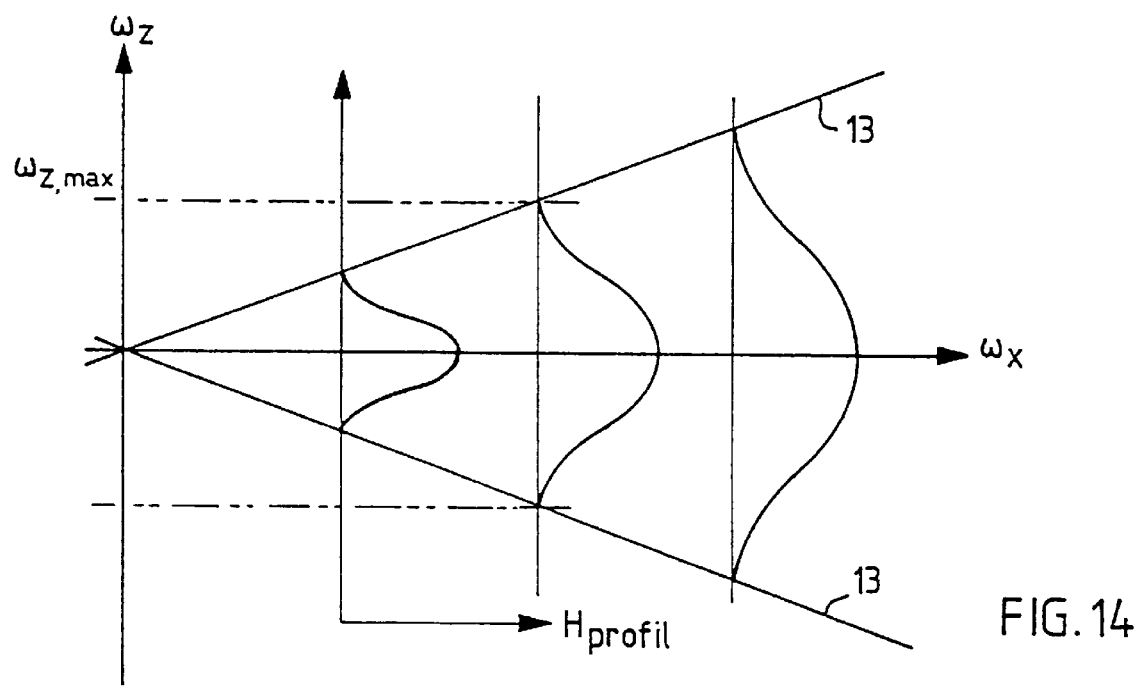

For a band-limited profile function $$H_{profile}(\omega_z) = 0 \text{ for } |\omega_z| > \omega_{z,max} \quad \text{(Eq. 12)}$$

the scanned locus frequency region is divided into a completely scanned region and an incompletely scanned region (see FIGS. 13, 14)

$$|\omega_x| < \omega_{z,max}/\tan\alpha \text{ incomplete scanning}$$

$$|\omega_x| < \omega_{z,max}/\tan\alpha \text{ incomplete scanning} \quad \text{(Eq. 13)}$$

In the region of the complete scanning, a homogenous slice profile forms that is independent of the locus frequency, and in the region of the incomplete scanning the profile function is cut off abruptly at the scan edges. However, the relations here are more advantageous than in approach (1), since the profile function at the scan boundary has already decayed to a certain extent. Nonetheless, the remaining jump still leads to an extensive oscillation characteristic of the slice profile. Structures foreign to the slice, from adjacent slices, can lead to artefacts in the reconstruction image. The abrupt breaking off at the scan edges can also lead to a formation of filter-caused overshootings.

(3) Smoothing of the Break-off Edges of Cut-off Profile Functions

With a locus-frequency-dependent scaling $$\omega_z \to \omega_z \cdot \min\left(1, \frac{\omega_{z,\max}}{|\omega_x| \cdot \tan\alpha}\right) \quad \text{(Eq. 14)}$$

the profile functions in the region of the incomplete scanning are compressed to the point at which at the scan limits they have already fallen to zero (see FIG. 13). Break-off edges at the scan boundaries are thereby avoided. However, due to the reduction of the effective width of the profile function, this approach can lead to an increase of the locus-frequency-dependent slice thickness.

(4) Scaling of the Profile Function for all Regions

An expansion of the above locus-frequency-dependent scaling to include the region of the complete scanning $$\omega_z \to \omega_z \cdot \frac{\omega_{z,\max}}{|\omega_x| \cdot \tan\alpha} \quad \text{(Eq. 15)}$$

leads, besides the known compression of the profile function in the region of incomplete scanning, to an extension in the region of complete scanning (see FIG. 14). The slice thickness for high locus frequencies is thereby improved.

(5) Projection-angle-dependent Weighting

For this method, a profile function is formulated that no longer depends on the z component of the locus frequency, but rather on the angle component $\omega_\phi$. According to the Fourier slice theorem, in the 3D Fourier space the entries of a plane with constant angle component $\omega_\phi$ are obtained by a projection at the radiation angle $\phi = \omega_\phi$ (see FIGS. 10, 11).

with $\omega_\phi = -\arctan\left(\frac{\omega_z}{\omega_x}\right)$ $$H_{profile}(\omega_z) \to H_{profile}(\omega_\phi) \quad \text{(Eq. 16)}$$

The formal separation (Eq. 5) is cancelled here. However, a comparison with the approach of the scaling of the profile function for all regions (Eq. 15) shows that the projection-angle-dependent weighting of the scaling of the profile function is similar over all regions. For small tomosynthesis angles a, the two approaches even coincide with one another, since here, with $\omega_z/\omega_x \ll 1$, the approximation $\arctan(\omega_z/\omega_x) \approx \omega_z/\omega_x$ holds.

This formulation advantageously prepares the way for a simple method for increasing contrast, which is described below.

(6) Increased-contrast. Projection-angle-dependent Weighting

In tomosynthesis, components with low locus frequency are not scanned sufficiently. The low-locus-frequency image components are strongly damped after the inversion, by approximation, of the transmission function (Eq. 4), which leads to a decrease of contrast. Measures for removing the slice feed-through lead to a further attenuation of these portions. In the general specification, for compensation an approximate equal weighting of all locus frequency components by means of a corresponding manipulation of the spectral function was proposed. Alternatively, here portions of non-inverted projection images are mixed into the locus frequency regions, in which the profile function takes away portions of the inverted projection images $$H_{filter}(\vec{\phi}) = [H_{profile}(\omega_\phi) \cdot H_{inv}(\omega_x, \omega_z) + \eta \cdot (1 - H_{profile}(\omega_\phi))] \cdot H_{spectrum}(\omega_x, \omega_y) \quad \text{(Eq. 17)}$$

The mixing coefficient $\eta$ determines the degree of increase of contrast, which however cannot be increased arbitrarily. As the mixing coefficient increases, the non-inverted image portions dominate, and lead the reconstruction image back to the level of the simple back-projection. The image impression becomes increasingly washed-out, and the blurrings prevent the increases in intensity from being able to develop into increases in contrast.

An interesting possibility for the realization of the method offers itself here. Two reconstruction volumes of the same dimension are reconstructed. The individual projection images contribute to the one reconstruction volume with a weight $H_{profile}(\omega_\phi)$, and are filtered with the inverse 3D transmission function. The individual projection images enter unfiltered into the other reconstruction volume, with a weight $(1 - H_{profile}(\omega_\phi))$. Subsequently, the two reconstruction volumes are mixed by superposition according to the mixing coefficient n, and the superposed tomogram is post-filtered with the spectral function. In this type of realization, the contrast-increasing mixing, as a type of grey-scale windowing, could be modified subsequently until a subjectively good image impression arises.

As already shown in approach (1), the computing expense in the application of the 2D filter of the spectral function can be reduced by means of an efficient approximative implementation (e.g. short filter kernels in the spatial domain). In the approximation of small tomosynthesis angles, the filtering can be carried out with the inverse (by approximation) 3D transmission function (Eq. 4) as a post-processing at the tomogram of the reconstruction volume, back-projected with the weights $H_{profile}(\omega_\phi)$, and can likewise be implemented approximatively and efficiently.

In an X-ray-table-like arrangement with detectors parallel to the tomograms, there is another simple possible realization. According to the scaling rule of the detector coordinate axes given oblique incidence (Eq. 9), in the approximation of small tomosynthesis angles (Eq. 4) the 2D filtering function of the projection images is written according to Eq. 10

$$\tilde{H}_{filter,\phi}^{2D}(\omega_u, \omega_v) = [H_{profile}(\phi) \cdot H_{inv}(\omega_u) = \eta \cdot (1 - H_{profile}(\phi))] \cdot H_{spectrum}(\omega_u, \omega_v) \quad \text{(Eq. 18)}$$

The projection image filtered with the inverse 3D transmission function is mixed in projection-angle-dependent fashion with the original projection image, is filtered with the spectral function, and is subsequently back-projected. The filtering functions of the inverse 3D transmission function and of the spectral function are independent of the projection angle. As above, a reduction of the computing expense can be achieved by means of an efficient, approximative implementation (e.g., short filter kernels in the spatial domain). Here as well, it is possible to carry out the filtering with the spectral function in the reconstructed tomograms.

In the following, as an example an embodiment from transmission tomography is specified.

The embodiment for transmission tomography with linear scanning and an X-ray-table-like arrangement (see image 9) consists of the components already specified in the context of the embodiment of FIG. 1, but here a means for linear displacement of the detector and the X-ray source on a straight line is used.

For the embodiment, the approach (6), "Increased-contrast, projection-angle-dependent weighting" with a filtering function is selected, consisting of the following components:

Approximation of small tomosynthesis angles (Eq. 4) for the inverse 3D transmission function Projection-angle-dependent profile function as $$H_{profile}(\omega_\varphi) = \frac{\sin\left(\frac{\omega_\varphi}{\alpha} \cdot \pi\right)}{\frac{\omega_\varphi}{\alpha} \cdot \pi} \text{ for } |\omega_\varphi| \leq \alpha$$

$H_{profile}(\omega_\varphi) = 0$ otherwise

Constant spectral function $H_{spectrum}(\omega_x, \omega_y) \equiv 1$

The 2D filtering $H_{filter,\omega}^{2D}(\omega_u, \omega_v)$ function of the projection images is calculated according to Eq. 18. The actual reconstruction at the image computer takes place according to the following procedure: for each projection angle ω, the associated projection image $p_\phi(u,v)$ is filtered with the inverse 3D transmission function $H_{inv}(\omega_u)$. This takes place in the locus space by means of 1D convolution of the projection image $p_\phi(u,v)$ with the Fourier back-transform $h_{inv}(u)$ of the inverse 3D transmission function. Since all the projection images are filtered with the same convolution kernel $h_{inv}(u)$, this kernel need be calculated only once, and can also be implemented in computing-efficient fashion by means of suitable approximations. The projection images $\tilde{p}_\phi(u, v)$ filtered in this way are superposed, with the corresponding weightings according to Eq. 18, with the unfiltered projection images $p_\phi(u,v)$ to form projection images $\tilde{p}_\phi(u, v)$. The 3D reconstruction image g(x,y,z) is calculated by back-projection of the superposed projection images $\tilde{p}_\phi(u, v)$. A generally known standard method is used for the back-projection, e.g. a voxel-driven back-projector that determines for each voxel the corresponding superposed projection values and increments the voxel value thereby.

In addition, the invention can also be applied in nuclear medicine (emission tomography). In this case, tomosynthetic scanning (e.g. circular or linear) is produced, as is known, by a specific collimator that releases only the radiation paths to the detector that correspond to the selected scanning cf. e.g. [S. Dale, M. Holmberg, J. Persson, T. Ribbe, H. Elmqvist, D. Bone, L.-A. Brodin, C. Lindström and L. Jorfeldt, "A Mobile Tomographic Gamma Camera System for Acute Studies," IEEE Trans. on Nucl. Science 44 (1997), 199–203].

Although modifications and changes may be suggested by those skilled in the art, it is the intention of the inventors to embody within the patent warranted hereon all changes and modifications as reasonably and properly come within the scope of their contribution to the art.

We claim as my invention:

1. A tomosynthesis method for reconstructing a three-dimensional image of an object, comprising the steps of:
    providing an x-ray source having an x-ray focus;
    providing a radiation detector;
    disposing a three-dimensional object in a three-dimensional object space between said x-ray focus and said radiation detector;
    scanning said object by moving at least said x-ray focus relative to said object to irradiate said object with x-rays from a plurality of different projection angles φ;
    detecting said x-rays attenuated by said object with said radiation detector at each of said projection angles φ as respective projection images in a 2D recording geometry, each of said projection images comprising a set of projection image data of said object in a 2D projection image space;
    applying a 2D filtering function $H^{2D}_{filter,\phi}(\omega_u, \omega_v)$ to said sets of projection image data to obtain filtered sets of projection image data;
    in a computer, individually back-projecting said filtered sets of projection image data into a 3D reconstruction image volume for producing a reconstruction image of said object; and
    determining said 2D filtering function by the steps of:
        calculating a 3D transmission function $H_{proj}(\omega_x, \omega_y, \omega_z)$ from the recording geometry for the individual sets of projection image data and back-projecting the individual sets of projection image data into the 3D reconstruction image volume;
        inverting by approximation, the 3D transmission function $H_{proj}(\omega_x, \omega_y, \omega_z)$ and thereby determining an inversion function $H_{inv}(\omega_x, \omega_y, \omega_z)$;
        producing a 3D filtering function $H_{opt}(\omega_x, \omega_y, \omega_z)$ dependent on at least one selected image characteristic of the reconstruction image;
        determining a resulting 3D filtering function $H_{filter}(\omega_x, \omega_y, \omega_z)$ by multiplying the 3D filtering function $H_{opt}(\omega_x, \omega_y, \omega_z)$ and the inversion function $H_{inv}(\omega_x, \omega_y, \omega_z)$; and
        determining said 2D filtering function $H^{2D}_{filter,\phi}(\omega_u, \omega_v)$ from the resulting 3D filtering function $H_{filter}(\omega_x, \omega_y, \omega_z)$ by coordinate transformation of the 3D object space into the 2D projection image space of the respective individual sets of projection image data at the projection angles φ.

2. A method as claimed in claim 1 wherein the step of scanning said object comprises scanning said object by moving at least said x-ray focus along a linear scanning path.

3. A method as claimed in claim 2 comprising the additional steps of:
    approximating said 3D filtering function $H_{proj}(\omega_x, \omega_y, \omega_z)$ as a resulting 3D filtering function $H_{filter}(\omega_x, \omega_y, \omega_z)$, independent of $\omega_z$; and
    using said resulting 3D filtering function $H_{filter}(\omega_x, \omega_y)$ as said 2D filtering function for filtering said projection image data sets to obtain said filtered sets of projection image data.

4. A method as claimed in claim 3 comprising the additional steps of:
    identifying at least one selected tomogram in said 3D reconstruction volume; and
    applying said resulting 3D filtering function $H_{filter}(\omega_x, \omega_y)$ as said 2D filtering function only to filter said projection image data sets for said at least one selected tomogram.

5. A method as claimed in claim 4 comprising the additional steps of:
    providing a display monitor; and
    immediately displaying said at least one selected tomogram on said display monitor after producing said reconstruction image thereof.

6. A method as claimed in claim 1 wherein the step of scanning said object comprises scanning said object by moving at least said x-ray focus relative to said object in a circular scanning path.

7. A method as claimed in claim 1 comprising the step of forming, by using said resulting 3D filtering function $H_{filter}(\omega_x, \omega_y, \omega_z)$, a substantially homogenous slice profile of said reconstruction image, at least in a sub-region of said object space.

8. A method as claimed in claim 1 wherein said object space includes an incompletely scanned region, and wherein said method comprises the additional steps of:
   forming a spectral function $H_{spectrum}(\omega_x,\omega_y)$ as a filter component of said resulting 3D filtering function $H_{filter}(\omega_x,\omega_y,\omega_z)$; and
   using said spectral function to eliminate all contributions to said reconstruction image arising from said incompletely scanned region.

9. A method as claimed in claim 1 wherein said object space includes an incompletely scanned region, and wherein said method comprises the additional steps of:
   forming a spectral function $H_{spectrum}(\omega_x,\omega_y)$ as a filter component of said resulting 3D filtering function $H_{filter}(\omega_x,\omega_y,\omega_z)$; and
   using said spectral function to give contributions from said incompletely scanned region a lower weight in said reconstruction image than contributions from other regions of said object space.

10. A method as claimed in claim 1 wherein said object space includes an incompletely scanned region which produces contributions having an inherent damping to said reconstruction image, said method comprising the additional steps of:
   forming a spectral function $H_{spectrum}(\omega_x,\omega_y)$ as a filter component of said resulting 3D filtering function $H_{filter}(\omega_x,\omega_y,\omega_z)$; and
   artificially equally weighting all contributions to said reconstruction image, including said contributions arising from said incompletely scanned region, for compensating for said inherent damping.

11. A method as claimed in claim 1 wherein said object space includes a scanned region which is scanned in the step of scanning said object, and wherein said scanned region has a scan edge, said scan edge producing a discontinuity in said reconstruction image, said method comprising the additional steps of:
   forming a profile function $H_{profile}(\omega_z)$ as one component of said resulting 3D filtering function $H_{filter}(\omega_x,\omega_y,\omega_z)$; and
   at least partially removing said discontinuities in said reconstruction image arising from said scan edge using said profile function $H_{profile}(\omega_z)$.

12. A method as claimed in claim 11 wherein the step of at least partially removing said discontinuities comprises multiplying said profile function $H_{profile}(\omega_z)$ with a window function having a value equal to one everywhere within said scanned region, except said edge region, and falls continuously to zero at boundaries which are still within said scanned region.

13. A method as claimed in claim 11 wherein the step of at least partially removing said discontinuities comprises conducting a convolution of said profile function $H_{profile}(\omega_z)$ with a smoothing convolution core.

14. A method as claimed in claim 11 wherein the step of at least partially removing said discontinuities comprises conducting a locus-frequency-dependent scaling of $\omega_z$ in said incompletely scanned region.

15. A method as claimed in claim 11 wherein the step of at least partially removing said discontinuities comprises a combination of scaling and smoothing contributions to said reconstruction image from said edge region using said profile function $H_{profile}(\omega_z)$.

16. A method as claimed in claim 1 comprising forming a profile function $H_{profile}(\omega_\phi)$, as said 3D filtering function, that is weighted dependent on said projection angle.

17. A mhethod as claimed in claim 16 comprising an increased contrast in said 3D reconstruction volume by using two identical sets of said projection images, processing said sets in different ways and afterwards mixing said sets, and filtering a first of said sets with an inverse 3D transfer function $H_{inv}(\omega_x, \omega_y, \omega_z)$ weighted by the profile function $H_{profile}(\omega_\phi)$, and weighting a second of said sets by a function $(1-H_{profile}(\omega_\phi))$.

18. A method as claimed in claim 17 wherein said object space includes two identically dimensioned reconstruction volumes, and wherein the step of producing a reconstruction image of said object comprises producing respective reconstruction images of said two reconstruction volumes, with individual ones of said projection images contributing to a first of said two reconstruction volumes with a weighting $H_{profile}(\omega_\phi)$ and which have been filtered with said inverse 3D transmission function $H_{inv}(\omega_x,\omega_y,\omega_z)$, and wherein individual ones of said projection images are employed without filtering thereof to contribute to a second of said two reconstruction volumes with a weighting of $1-H_{profile}(\omega_\phi))$, followed by mixing said two reconstruction volumes by superimposition with a mixing coefficient $\eta$.

19. A method as claimed in claim 18 wherein said two reconstruction volumes include at least one selected tomogram of said object selectable by selecting said mixing coefficient $\eta$, and wherein the step of mixing said two reconstruction volumes comprises mixing said two reconstruction volumes with a coefficient $\eta$ selected dependent on said selected tomogram.

20. A method as claimed in claim 19 comprising the additional step of immediately displaying said selected tomogram on a monitor.

21. A method as claimed in claim 1 wherein said reconstruction image includes a selected tomogram, and comprising the additional step of filtering said selected tomogram with a spectral function $H_{spectrum}(\omega_x,\omega_y)$ having a type an parameterization which are variable.

22. A method as claimed in claim 21 comprising the step of immediately displaying said selected tomogram on a monitor together with an identification of at least one of said type and said parameterization associated with said selected tomogram.

23. A method as claimed in claim 1 comprising the step of using said result 3D filtering function $H_{filter}(\omega_x, \omega_y, \omega_z)$, of if necessary, a further 3D filtering function, where a spatial-frequency-dependent scaling in the $\omega_z$ argument is conducted over the entire frequency region measured in the step of scanning said object.

24. A tomosynthesis method for reconstructing a three-dimensional image of an object, comprising the steps of:
   providing an x-ray source having an x-ray focus;
   providing a radiation detector;
   disposing a three-dimensional object in a three-dimensional object space between said x-ray focus and said radiation detector;
   scanning said object by moving at least said x-ray focus relative to said object to irradiate said object with x-rays from a plurality of different projection angles $\phi$;
   detecting said x-rays attenuated by said object with said radiation detector at each of said projection angles $\phi$ as respective projection images in a 2D recording geometry, each of said projection images comprising a set of projection image data of said object in a 2D projection image space;
   in a computer, individually back-projecting the said sets of projection image data into a 3D reconstruction image volume for producing a reconstruction image of said object;

applying a 3D filtering function $H_{filter}(\omega_x,\omega_y,\omega_z)$ to said reconstruction image of said object to obtain a filtered reconstruction image; and determining said 3D filtering function by the steps of:

calculating a 3D transmission function $H_{proj}(\omega_x,\omega_y,\omega_z)$ from the recording geometry for the individual sets of projection image data and back-projecting the individual sets of projection image data into the 3D reconstruction image volume;

inverting by approximation, the 3D transmission function $H_{proj}(\omega_x,\omega_y,\omega_z)$ and thereby determining an inversion function $H_{inv}(\omega_x,\omega_y,\omega_z)$;

producing a 3D filtering function $H_{opt}(\omega_x,\omega_y,\omega_z)$ dependent on at least one selected image characteristic of the reconstruction image;

determining a resulting 3D filtering function $H_{filter}(\omega_x,\omega_y,\omega_z)$ by multiplying the 3D filtering function $H_{opt}(\omega_x,\omega_y,\omega_z)$ and the inversion function $H_{inv}(\omega_x,\omega_y,\omega_z)$.

25. A method as claimed in claim 24 wherein the step of scanning said object comprises scanning said object by moving at least said x-ray focus along a linear scanning path.

26. A method as claimed in claim 25 comprising the additional steps of:

approximating said 3D filtering function $H_{proj}(\omega_x,\omega_y,\omega_z)$ as a resulting 3D filtering A function $H_{filter}(\omega_x,\omega_y,\omega_z)$, independent of $\omega_z$; and using said resulting 3D filtering function $H_{filter}(\omega_x,\omega_y)$ as said 2D filtering function for filtering said tomograms.

27. A method as claimed in claim 26 comprising the additional steps of:

identifying at least one selected tomogram in said 3D reconstruction volume; and applying said resulting 3D filtering function $H_{filter}(\omega_x,\omega_y)$ only to filter said at least one selected tomogram.

28. A method as claimed in claim 27 comprising the additional steps of:

providing a display monitor; and immediately displaying said at least one selected tomogram on said display monitor after producing said reconstruction image thereof.

29. A method as claimed in claim 24 wherein the step of scanning said object comprises scanning said object by moving at least said x-ray focus relative to said object in a circular scanning path.

30. A method as claimed in claim 24 comprising the step of forming, by using said resulting 3D filtering function $H_{filter}(\omega_x,\omega_y,\omega_z)$, a substantially homogenous slice profile of said reconstruction image, at least in a sub-region of said object space.

31. A method as claimed in claim 24 wherein said object space includes an incompletely scanned region, and wherein said method comprises the additional steps of:

forming a spectral function $H_{spectrum}(\omega_x,\omega_y)$ as a filter component of said resulting 3D filtering function $H_{filter}(\omega_x,\omega_y,\omega_z)$; and using said spectral function to eliminate all contributions to said reconstruction image arising from said incompletely scanned region.

32. A method as claimed in claim 24 wherein said object space includes an incompletely scanned region, and wherein said method comprises the additional steps of:

forming a spectral function $H_{spectrum}(\omega_x,\omega_y)$ as a filter component of said resulting 3D filtering function $H_{filter}(\omega_x,\omega_y,\omega_z)$; and using said spectral function to give contributions from said incompletely scanned region a lower weight in said reconstruction image than contributions from other regions of said object space.

33. A method as claimed in claim 24 wherein said object space includes an incompletely scanned region which produces contributions having an inherent damping to said reconstruction image, said method comprising the additional steps of:

forming a spectral function $H_{spectrum}(\omega_x,\omega_y)$ as a filter component of said resulting 3D filtering function $H_{filter}(\omega_x,\omega_y,\omega_z)$; and artificially equally weighting all contributions to said reconstruction image, including said contributions arising from said incompletely scanned region, for compensating for said inherent damping.

34. A method as claimed in claim 24 wherein said object space includes a scanned region which is scanned in the step of scanning said object, and wherein said scanned region has a scan edge, said scan edge producing a discontinuity in said reconstruction image, said method comprising the additional steps of:

forming a profile function $H_{profile}(\omega_z)$ as one component of said resulting 3D filtering function $H_{filter}(\omega_x,\omega_y,\omega_z)$; and at least partially removing said discontinuities in said reconstruction image arising from said scan edge using said profile function $H_{profile}(\omega_z)$.

35. A method as claimed in claim 34 wherein the step of at least partially removing said discontinuities comprises multiplying said profile function $H_{profile}(\omega_z)$ with a window function having a value equal to one everywhere within said scanned region, except said edge region, and falls continuously to zero at boundaries which are still within said scanned region.

36. A method as claimed in claim 34 wherein the step of at least partially removing said discontinuities comprises conducting a convolution of said profile function $H_{profile}(\omega_z)$ with a smoothing convolution core.

37. A method as claimed in claim 34 wherein the step of at least partially removing said discontinuities comprises conducting a locus-frequency-dependent scaling of $\omega_z$ in said incompletely scanned region.

38. A method as claimed in claim 34 wherein the step of at least partially removing said discontinuities comprises a combination of scaling and smoothing contributions to said reconstruction image from said edge region using said profile function $H_{profile}(\omega_z)$.

39. A method as claimed in claim 24 comprising forming a profile function $H_{profile}(\omega_\phi)$ as said 3D filtering function, that is weighted dependent on said projection angle.

40. A method as claimed in claim 39 comprising an increased contrast in said 3D reconstruction volume by filtering said 3D reconstruction volume with a filter consisting of $$(1-H_{profile}(\omega_\phi))+H_{profile}(\omega_\phi)H_{inv}(\omega_x,\omega_y,\omega_z).$$

41. A method as claimed in claim 37 wherein said object space includes two identically dimensioned reconstruction volumes, and wherein the step of producing a reconstruction image of said object comprises producing respective reconstruction images of said two reconstruction volumes, with individual ones of said projection images contributing to a first of said two reconstruction volumes filtered by $H_{profile}(\omega_\phi)$ and with said inverse 3D transmission function $H_{inv}(\omega_x,\omega_y,\omega_z)$, and to a second of said two reconstruction volumes filtered by $(1-H_{profile}(\omega_\phi))$, followed by mixing said two reconstruction volumes by superimposition with a mixing coefficient $\eta$.

42. A method as claimed in claim 41 wherein said two reconstruction volumes include at least one selected tomogram of said object selectable by selecting said mixing coefficient η and wherein the step of mixing said two reconstruction volumes comprises mixing said two reconstruction volumes with a coefficient η selected dependent on said selected tomogram.

43. A method as claimed in claim 42 comprising the additional step of immediately displaying said selected tomogram on a monitor.

44. A method as claimed in claim 24 wherein said reconstruction image includes a selected tomogram, and comprising the additional step of filtering said selected tomogram with a spectral function $H_{spetrum}(\omega_x,\omega_y)$ having a type an parameterization which are variable.

45. A method as claimed in claim 44 comprising the step of immediately displaying said selected tomogram on a monitor together with an identification of at least one of said type and said parameterization associated with selected tomogram.

46. A method as claimed in claim 24 comprising the step of using said resulting 3D filtering function $H_{filter}(\omega_x, \omega_y, \omega_z)$, or if necessary, a further 3D filtering function, where a spatial-frequency-dependent scaling in the $\omega_z$ argument is conducted over the entire frequency region measured in the step of scanning said object.

47. A tomosynthesis apparatus for reconstructing a three-dimensional irmiage of an object, comprising:

an x-ray source having an x-ray focus;

a radiation detector disposed to detect x-rays attenuated by a three-dimensional object in a three-dimensional object space between said x-ray focus and said radiation detector;

means for moving at least said x-ray focus relative to said object to scan said object by irradiating said object with x-rays from a plurality of different projection angles φ;

said radiation detector detecting said x-rays attenuated by said object with at each of said projection angles φ as respective projection images in a 2D recording geometry, each of said projection images comprising a set of projection image data of said object in a 2D projection image space;

means for applying a 2D filtering function $H^{2D}_{filter,\phi}(\omega_u, \omega_v)$ to said sets of projection image data to obtain filtered sets of projection image data;

computer means for individually back-projecting said filtered sets of projection image data into a 3D reconstruction image volume for producing a reconstruction image of said object; and said means for applying said 2D filtering function comprising means for determining said 2D filtering function by calculating a 3D transmission function $H_{proj}(\omega_x,\omega_y,\omega_z)$ from the recording geometry for the individual sets of projection image data and back-projecting the individual sets of projection image data into the 3D reconstruction image volume, thereby determining an inversion function $H_{inv}(\omega_x,\omega_y,\omega_z)$, producing a 3D filtering function $H_{opt}(\omega_x,\omega_y,\omega_z)$ dependent on at least one selected image characteristic of the reconstruction image, determining a resulting 3D filtering function $H_{filter}(\omega_x,\omega_y,\omega_z)$ by multiplying the 3D filtering function $H_{opt}(\omega_x,\omega_y,\omega_z)$ and the inversion function $H_{inv}(\omega_x,\omega_y,\omega_z)$, and determining said 2D filtering function $H^{2D}_{filter,\phi}(\omega_u,\omega_v)$ frorn the resulting 3D filtering function $H_{filter}(\omega_x,\omega_y,\omega_z)$ by coordinate transformation of the 3D object space into the 2D projection image space of the respective individual sets of projection image data at the projection angles φ.

48. A tomosynthesis apparatus as claimed in claim 47 wherein said computer means comprises said means for applying a 2D filtering function.

49. A tomosynthesis apparatus for reconstructing a three-dimensional image of an object, comprising:

an x-ray source having an x-ray focus;

a radiation detector disposed to detect x-rays attenuated by a three-dimensional object in a three-dimensional object space between said x-ray focus and said radiation detector;

means for moving at least said x-ray focus relative to said object to scan said object by irradiating said object with x-rays from a plurality of different projection angles said radiation detector detecting said x-rays attenuated by said object with at each of said projection angles φ as respective projection images in a 2D recording geometry, each of said projection images comprising a set of projection image data of said object in a 2D projection image space;

computer means for individually back-projecting said sets of projection image data into a 3D reconstruction image volume for producing a reconstruction image of said object;

means for applying a 3D filtering function $H_{filter}(\omega_x,\omega_y,\omega_z)$ to said reconstruction image of said object to obtain a filtered reconstruction object; and said means for applying said 3D filtering function comprising means for determining said 3D filtering function by calculating a 3D transmission function $H_{proj}(\omega_x,\omega_y,\omega_z)$ from the recording geometry for the individual sets of projection image data and back-projecting the individual sets of projection image data into the 3D reconstruction image volume, inverting by approximation, the 3D transmission function $H_{proj}(\omega_x,\omega_y,\omega_z)$ and thereby determining an inversion function $H_{inv}(\omega_x,\omega_y,\omega_z)$, producing a 3D filtering function $H_{opt}(\omega_x,\omega_y,\omega_z)$ dependent on at least one selected image characteristic of the reconstruction image, and determining a resulting 3D filtering function $H_{filter}(\omega_x,\omega_y,\omega_z)$ by multiplying the 3D filtering function $H_{opt}(\omega_x,\omega_y,\omega_z)$ and the inversion function $H_{inv}(\omega_x,\omega_y,\omega_z)$ and determining a resulting 3D filtering function $H_{filter,\phi}(\omega_x,\omega_y,\omega_z$ by multiplying the 3D filtering function $H_{filter}((\omega_x,\omega_y,\omega_z)$, and the inversion function $H_{inv}(\omega_x,\omega_y,\omega_z)$.

50. A tomosynthesis apparatus as claimed in claim 49 wherein said computer means comprises said means for applying a 3D filtering function.

* * * * *